United States Patent
Ward et al.

(10) Patent No.: US 10,751,494 B2
(45) Date of Patent: *Aug. 25, 2020

(54) PREVENTION OF VENTILATOR ASSOCIATED PNEUMONIA (VAP)

(71) Applicant: Virginia Commonwealth University, Richmond, VA (US)

(72) Inventors: Kevin R. Ward, Superior Township, MI (US); Curtis N. Sessler, Richmond, VA (US); Mary Jo Grap, Midlothianq, VA (US); Laurence J. DiNardo, Richmond, VA (US); Bruce D. Spiess, Manakin Sabot, VA (US); Rao R. Ivatury, Richmond, VA (US); Cindy Munro, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 516 days.

This patent is subject to a terminal disclaimer.

(21) Appl. No.: 15/274,725

(22) Filed: Sep. 23, 2016

(65) Prior Publication Data

US 2017/0007791 A1    Jan. 12, 2017

Related U.S. Application Data

(63) Continuation of application No. 13/181,843, filed on Jul. 13, 2011, now Pat. No. 9,457,163, which is a
(Continued)

(51) Int. Cl.
*A61M 16/04* (2006.01)

(52) U.S. Cl.
CPC .......... *A61M 16/049* (2014.02); *A61M 16/04* (2013.01); *A61M 16/0434* (2013.01);
(Continued)

(58) Field of Classification Search
CPC .............. A61M 16/04; A61M 16/0463; A61M 16/0488; A61M 16/049; A61M 16/0493;
(Continued)

(56) References Cited

U.S. PATENT DOCUMENTS

| 518,810 A | 4/1894 | Miles et al. |
| 2,702,032 A | 2/1955 | Freedland |

(Continued)

OTHER PUBLICATIONS

Hartmann et al., Reduction of the bacterial load by the silver-coated endotracheal tube (SCET), a laboratory investigation, Technol. Health Care, 7(5):359-70 (1999).
(Continued)

*Primary Examiner* — Joseph D. Boecker
(74) *Attorney, Agent, or Firm* — Marshall, Gerstein & Borun LLP

(57) ABSTRACT

Ventilator associated pneumonia (VAP) may be prevented in a patient, or its occurrence reduced in a population of patients, by using an anti-VAP device or an anti-VAP material such as an anti-VAP mouthpiece that absorbs secretions. By reducing the problem of bacterial-containing secretions that otherwise build up in the airway of, and elsewhere in, the intubated patient, VAP can be prevented from occurring in intubated patients, such as patients intubated with an endotracheal tube (ETT) or a nasogastric tube. Anti-VAP mouthpieces also are useable in non-intubated patients to maintain oral hygiene.

17 Claims, 20 Drawing Sheets

Related U.S. Application Data continuation-in-part of application No. 11/217,667, filed on Sep. 2, 2005, now Pat. No. 8,042,544.

(60) Provisional application No. 60/607,070, filed on Sep. 3, 2004.

(52) U.S. Cl.
CPC .... *A61M 16/0436* (2014.02); *A61M 16/0479* (2014.02); *A61M 2205/0205* (2013.01)

(58) Field of Classification Search
CPC ...... A61M 16/0495; A61M 2205/0205; A61C 5/82; A61C 5/90
See application file for complete search history.

(56) References Cited

U.S. PATENT DOCUMENTS

| | | |
|---|---|---|
| 3,481,339 A | 12/1969 | Millet |
| 3,638,655 A | 2/1972 | Doherty |
| 4,091,816 A | 5/1978 | Elam |
| 4,233,025 A | 11/1980 | Larson et al. |
| 4,976,261 A | 12/1990 | Gluck et al. |
| 5,033,466 A | 7/1991 | Weymuller, Jr. |
| 5,065,755 A | 11/1991 | Klafta |
| 5,078,604 A | 1/1992 | Malmin |
| 5,188,630 A | 2/1993 | Christoudias |
| 5,230,332 A | 7/1993 | Strickland |
| 5,236,415 A | 8/1993 | Stallings |
| 5,285,777 A | 2/1994 | Beckwith |
| 5,364,358 A | 11/1994 | Hewitt et al. |
| 5,370,656 A | 12/1994 | Shevel |
| 5,501,215 A | 3/1996 | Huerta |
| 5,524,642 A | 6/1996 | Rosenblatt |
| 5,582,167 A | 12/1996 | Joseph |
| 5,599,304 A | 2/1997 | Shaari |
| 5,626,128 A * | 5/1997 | Bradley ............ A61M 16/0488 128/200.26 |
| 5,709,691 A | 1/1998 | Morejon |
| 5,819,723 A | 10/1998 | Joseph |
| 5,937,861 A | 8/1999 | Augustine |
| 6,082,361 A | 7/2000 | Morejon |
| 6,443,147 B1 | 9/2002 | Matter |
| 6,745,773 B1 | 6/2004 | Gobel |
| 7,044,929 B2 | 5/2006 | Vanskiver et al. |
| 7,258,120 B2 | 8/2007 | Melker |
| 9,457,163 B2 * | 10/2016 | Ward .................... A61M 16/04 |
| 2003/0039942 A1 * | 2/2003 | Phillips .................. A61C 5/90 433/140 |
| 2003/0055474 A1 | 3/2003 | VanSkiver et al. |
| 2003/0073625 A1 | 4/2003 | Redman et al. |
| 2003/0170590 A1 * | 9/2003 | Heck ........................ A61C 5/90 433/140 |
| 2004/0011358 A1 | 1/2004 | Smaldone et al. |
| 2004/0079376 A1 | 4/2004 | Melker |
| 2004/0110738 A1 * | 6/2004 | Gillis ...................... A61F 13/36 514/184 |
| 2004/0161447 A1 | 8/2004 | Paul |
| 2004/0220534 A1 | 11/2004 | Martens et al. |
| 2005/0054784 A1 | 3/2005 | Qin et al. |
| 2005/0065141 A1 | 3/2005 | Odink et al. |
| 2006/0096600 A1 * | 5/2006 | Witt .................. A61M 16/0488 128/848 |
| 2006/0140984 A1 | 6/2006 | Tamarkin et al. |
| 2008/0011304 A1 | 1/2008 | Stewart |
| 2013/0146068 A1 * | 6/2013 | Van Wagenen ... A61M 16/0497 128/862 |
| 2014/0041673 A1 * | 2/2014 | Walters ............ A61B 17/12104 128/887 |
| 2014/0048079 A1 * | 2/2014 | Gardner ............ A61M 16/0497 128/860 |

OTHER PUBLICATIONS

Kollef et al., A randomized clinical trial of continuous aspiration of subglottic secretions in cardiac surgery patients, Chest, 116(5):1339-46 (1999).
Livingston, Prevention of ventilator-associated pneumonia, Am. J. Surg., 179(2A Suppl):12S-17S (2000).
Morehead et al., Ventilator-associated pneumonia, Arch. Intern. Med., 160(13):1926-36 (2000).
Reali-Forster et al., New ultrathin-walled endotracheal tube with a novel laryngeal seal design. Long-term evaluation in sheep, Anesthesiology, 84(1):162-72 (1996).
Seegobin, Aspiration beyond endotracheal cuffs, Can. Anaesth. Soc. J., 45:273-9 (1986).
Shorr, et al. "Continuous Subglottic Suctioning for the Prevention of Ventilator-Associated Pneumonia: Potential Economic Implications," Chest 119:228-35 (2001).
Valles et al., Continuous aspiration of subglottic secretions in preventing ventilator-associated pneumonia, Ann. Intern. Med., 122(3):179-86 (1995).
Young et al., Compliance characteristics of the Portex Soft Seal Cuff improves seal against leakage of fluid in a pig trachea model, Crit. Care, 3(5):123-6 (1999).
Young et al., Evaluation of a new design of tracheal tube cuff to prevent leakage of fluid to the lungs, Br. J. Anaesth., 80(6):796-9 (1998).
Young et al., Prevention of tracheal aspiration using the pressure-limited tracheal tube cuff, Anaesthesia, 54(6):559-63 (1999).
Young et al., The prevention of pulmonary aspiration with control of tracheal wall pressure using a silicone cuff, Anaesth. Intensive Care, 28(6):660-5 (2000).
Young et al., Ventilator-associated pneumonia. Diagnosis, pathogenesis and prevention, Anaesthesia, 54(12):1183-97 (1999).

\* cited by examiner

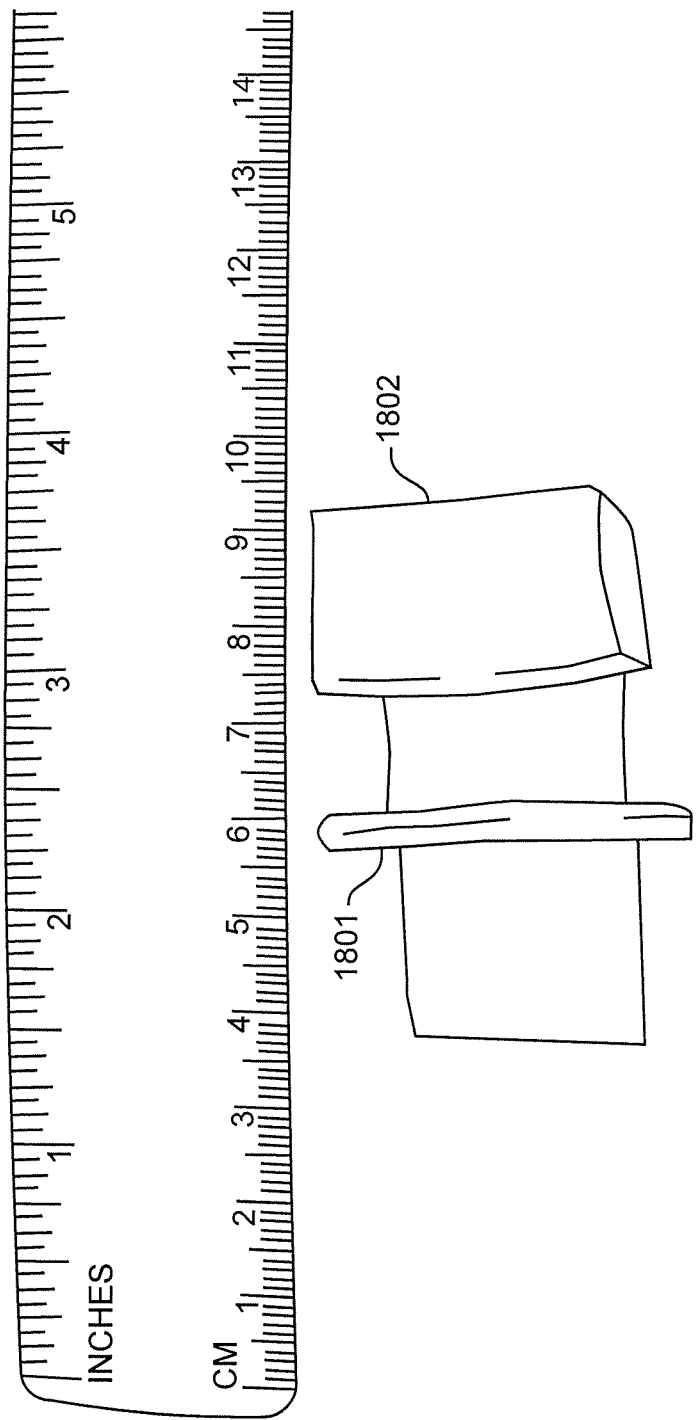

PREVENTION OF VENTILATOR ASSOCIATED PNEUMONIA (VAP)

RELATED APPLICATIONS

This is a continuation of U.S. application Ser. No. 13/181,843, filed Jul. 13, 2011, entitled "Prevention of Ventilator Associated Pneumonia (VAP)", which is a continuation-in-part of U.S. application Ser. No. 11/217,667, filed Sep. 2, 2005, entitled "Prevention of Ventilator Associated Pneumonia (VAP)", which claims the benefit of U.S. Provisional Application No. 60/607,070, filed Sep. 3, 2004, entitled "Device and Methods to Prevent Ventilator Associated Pneumonia and to Provide Laryngeal Anesthesia During Mechanical Ventilation."

FIELD OF THE INVENTION

This invention relates to treatment of patients who are intubated with an endotracheal tube (ETT), and especially to ventilator associated pneumonia (VAP) undesirably associated with such intubation.

BACKGROUND OF THE INVENTION

Ventilator associated pneumonia (VAP) is a potentially preventable cause of pneumonia that occurs in patients who are endotracheally intubated and mechanically ventilated for more than 48 hours. VAP may occur in up to 65% of patients in the intensive care unit (ICU) and is associated with an increase in morbidity and mortality. It is estimated that cost of diagnosing and treating VAP exceeds 1.1 billion dollars annually. Young P J, Ridley S A, Ventilator-associated pneumonia, Diagnosis, pathogenesis and prevention, Anaesthesia 1999; 54(12):1183-97; Morehead R S, Pinto S J, Ventilator-associated pneumonia, Arch Intern Med 2000; 160(13):1926-36.

VAP is usually a bacterial nosocomial pneumonia, which was neither present nor incubating at the time of endotracheal intubation. Causes of VAP are multifactorial (FIG. 1). The diagnosis of VAP is difficult and expensive. Controversy continues to exist in the methodology in making a definitive diagnosis. Treatment is also controversial and the use of empiric antibiotics is believed to have contributed to making the overall treatment of true VAP more difficult. Patients developing VAP require additional testing to make the diagnosis and additional treatments. A major cost to the treatment is prolonging the time patients require mechanical ventilation and thus care in the ICU setting. This increased time of treatment in this setting is likely to actually increase the chances of additional complications including developing additional VAPs and antibiotic resistant organisms.

The microbiology of VAP consist of a combination of Gram positive, Gram negative, and anaerobic organisms, most of which are ororpharyngeal or enteric in origin. As such a major mechanism believed to be responsible for the development of VAP is the microaspiration of pooled oropharyngeal secretions around the inflated cuff of an endotracheal tube (FIG. 2).

Despite the use of high volume low pressure (HVLP) endotracheal tube cuffs, there is clear evidence that small channels develop between the endotracheal tube cuff and the trachea, which allow passage of subglottic secretions into the lower respiratory tract. These channels develop because small folds develop from incomplete expansion of the endotracheal tube cuff. Seegobin R D, van Hasselt G L, Aspiration beyond endotracheal cuffs, Can Anaesth Soc J 1986; 33(3 Pt 1):273-9. The number of the folds or channels can be reduced if higher volumes are used to inflate the cuffs. However, higher volumes will result in higher pressures being created between the cuff and the tracheal mucosa thus placing the tracheal mucosa at risk for necrosis.

One strategy to reduce VAP from pooled secretions has been to perform continuous aspiration of subglottic secretions (CASS). A specially designed endotracheal tube called the HI-LO® EVAC tube by Mallinckrodt allows for this. This endotracheal tube contains a separate dorsal lumen ending in the subglottic space just above HVLP cuff. Fluid can be drained along this channel with suction. When clinically studied, the incidence of VAP has been reduced from 29% to 13% with intermittent drainage and 32% to 18% with continuous drainage. (Valles J, Artigas A, Rello J, Bonsoms N, Fontanals D, Blanch L, et al., Continuous aspiration of subglottic secretions in preventing ventilator-associated pneumonia, Ann Intern Med 1995; 122(3):179-86; Kollef M H, Skubas N J, Sundt T M, A randomized clinical trial of continuous aspiration of subglottic secretions in cardiac surgery patients, Chest 1999; 116(5):1339-46.) The method appears to result in major cost savings if its use were wide spread. (Shorr A F, O'Malley P G, Continuous Subglottic Suctioning for the Prevention of Ventilator-Associated Pneumonia: Potential Economic Implications, Chest 2001; 119:228-35.) The disadvantage of this method is that suction is required. Because endotracheal intubation occurs in many non-ICU areas, suction is not readily available. Patients are likely to be a most risk for aspiration from subglottic secretions very early after intubation especially when it is performed in less than ideal places such as on the wards, the emergency department, or in the prehospital setting. For example, over 55% of head-injured patients requiring intubation in the field or emergency department development pneumonia which might be from very early aspiration. (Livingston D H, Prevention of ventilator-associated pneumonia, Am J Surg 2000; 179(2A Suppl):12S-17S.) Furthermore, patients often require movement from the ICU to other locations within the hospital in order to undergo additional treatments or diagnostic studies. Continuous suction may not be available during these times. In addition, maneuvers such as changing patient position in a bed may serve to increase balloon channel size or relationship between the HI-LO EVAC port and the pooled secretions thus creating additional opportunity for aspiration.

A number of methods, which involve changes in cuff design, have reported various degrees of success but none have undergone extensive clinical testing. One method has used a latex cuff, which appears to provide the sealing effectiveness of low volume high pressure cuffs without damage to the tracheal wall. (Young P J, Ridley S A, Downward G., Evaluation of a new design of tracheal tube cuff to prevent leakage of fluid to the lungs, Br J Anaesth 1998; 80(6):796-9.) The addition of keeping the cuff at a constant pressure using a special inflation system adds to the degree of protection. (Young P J, Basson C, Hamilton D, Ridley S A, Prevention of tracheal aspiration using the pressure-limited tracheal tube cuff, Anaesthesia 1999; 54(6):559-63.) A modification of this cuff using silicone has been studied in humans requiring tracheostomy and appears to decrease leakage of supraglottic fluid compared conventional HVLP cuffs. (Young P J, Burchett K, Harvey I, Blunt M C, The prevention of pulmonary aspiration with control of tracheal wall pressure using a silicone cuff, Anaesth Intensive Care 2000; 28(6):660-5.) This tube and cuff are manufactured by Euromedical Industries and have been used as part of the intubating laryngeal mask system.

Another cuff called the Portex Soft Seal HVLP cuff (Portex Ltd, Hythe UK) has been tested against other HVLP cuffs in bench models and appears to perform better in terms of reducing leakage around the cuff. (Young P J, Blunt M C, Compliance characteristics of the Portex Soft Seal Cuff improves seal against leakage of fluid in a pig trachea model, Crit Care (Lond) 1999; 3(5):123-26.)

Also a unique thin walled endotracheal tube has been designed in which a traditional air filled cuff is replaced by a series of circumferential gills. During intubation, the tube is placed so that a number of the gills are above and below the vocal cords. This creates a seal for positive pressure ventilation (up to 40 cm H2O of peak inspiratory pressure) as well as a barrier to supraglottic secretions. (Reali-Forster C, Kolobow T, Giacomini M, Hayashi T, Horiba K, Ferrans V J, New ultrathin-walled endotracheal tube with a novel laryngeal seal design: Long-term evaluation in sheep, Anesthesiology 1996; 84(1):162-72; discussion 27A.) Although tested in animals we are not aware of any clinical testing. It is unknown what type of reaction might be caused by the gills coming in contact with the vocal cords in terms of irritation.

Other device strategies to reduce or prevent VAP have been to embed the endotracheal tube with antimicrobials such as silver. This method appears to reduce the bacterial load. (Hartmann M, Guttmann J, Muller B, Hallmann T, Geiger K, Reduction of the bacterial load by the silver-coated endotracheal tube (SCET), a laboratory investigation, Technol Health Care 1999; 7(5):359-70) However, it is presumed that the secretions must be in contact with the silver for sufficient periods of time for its antimicrobial activity to be effective. In regards to this, intubation done in less than ideal circumstances where patients may be at greatest risk for microaspiration means that antibiotic embedded systems or tubes designed to prevent formation of biofilm might not be effective in this time early time range.

Another major problem in the patient requiring endotracheal intubation and mechanical ventilation is the need for sedation due to the coughing reflexes induced by contact of the endotracheal tube and cuff with points of the supra and subglottic portions of the larynx. These points include the epiglottis, vocal cords, and tracheal mucosa. These reflexes are capable of producing such irritation and coughing as to require significant systemic sedation. This degree of additional sedation can impede physical and neurologic assessment of the patient and delay efforts for weaning of mechanical ventilation. This is of great importance because additional time spent utilizing mechanical ventilation will necessarily result in the incurrence of significant expense and may potentially result in the development of VAP with all of its complications and additional expense.

Methods/devices used to reduce the coughing reflex associated with endotracheal tubes include instilling local anesthetics through the lumen of the endotracheal tube. This method is believed to anesthetize to carina of the tracheal-bronchial tree. One device was found on the internet, which depicts a multilumen endotracheal tube allowing for instillation of anesthetic agents such as lidocaine. These ports appear to end at various locations along the tracheal bronchial tree. It is assumed that intermittent administration and contact of anesthesia at these points will provide sufficient anesthesia of the tracheal bronchial tree in contact with the endotracheal tube as to significantly blunt the coughing reflex.

Patent literature about prevention and/or reduction of ventilator associated pneumonia is as follows.

U.S. Patent Application No. 20030073625 was published Apr. 17, 2003, by Redman et al., for "Methods of preventing ventilator associated pneumonia by oral administration of antimicrobial IB-367 peptides."

U.S. Patent Application No. 20040079376 was published Apr. 29, 2004, by Melker, for "Endotracheal tube apparatus and method for using the same to reduce the risk of infections." A tube-in-tube endotracheal tube apparatus is disclosed.

U.S. Patent Application No. 20050065141 was published Mar. 24, 2005, by Odlink et al., for "Carbapenems useful in treating and preventing pulmonary infections, pharmaceutical compositions thereof and modes of administration thereof."

Conventional strategies to reduce VAP necessitate purchase of a separate endotracheal tube, which making implementation difficult especially if VAP prevention strategies are to be performed in all settings at the earliest possible time. In addition, each conventional strategy is relatively singular or limited in its ability to prevent VAP.

Also, in a well-known and practiced conventional approach for reducing VAP, nursing and support staff perform repetitive dental and oral hygiene on an intubated patient to attempt to address VAP-causing organisms present in and on the patient's dentition including the gums (gingival) and nearby mucosa. However, this manual hygiene work on intubated patients is labor-intensive, and even so some of them still develop VAP. Use of such techniques in the early stages of intubation such as in the pre-hospital and emergency department settings is not practical. This is unfortunate because these are places where patients are at major risks and where the normal microbial oral flora of the patient rapidly changes to more virulent hospital-based pathogens.

SUMMARY OF THE INVENTION

The above problems and shortcomings have been addressed by the present invention. The present inventors have recognized that ventilator associated pneumonia (VAP) may be prevented in a patient (such as, e.g., a human patient, a veterinary patient), or its occurrence reduced in a population of patients, by using a relatively-simple anti-VAP device or an anti-VAP material in a space that otherwise would be where bacterial-containing secretions would form. By reducing the problem of bacterial-containing secretions that otherwise build up in the airway of the intubated patient, VAP can be prevented from occurring in intubated patients.

In one preferred embodiment, the invention provides an anti-VAP system, comprising an anti-VAP device or an anti-VAP material, wherein the device or the material is sized and configured to be disposed in a patient airway which is intubated with an endotracheal tube (ETT), such as, e.g., an anti-VAP system comprising a device attached or attachable to the ETT; an anti-VAP system wherein the device or the material is touching the ETT; an anti-VAP system wherein the device or the material is in proximity to the ETT; an anti-VAP system wherein the device or the material is situated within a distance of 1 cm or closer to where secretions build up in the airway of the intubated patient; an anti-VAP system comprising an anti-VAP attachment mechanically attachable to, and detachable from, the ETT; an anti-VAP system comprising a device that is a sponge or is spongy; an anti-VAP system comprising a foamable material; an anti-VAP system comprising a semi-solid or a gel; an anti-VAP system wherein the device or the material remains in the patient airway for at least an hour; an anti-VAP system wherein the device or the material comprises at least one selected from the group consisting of: an absorbing agent; an antibacterial agent; and an anesthetic agent; an anti-VAP system wherein the device or the material is removable from the ETT separately without requiring removal of the ETT; an anti-VAP system comprising an anti-VAP attachment configured to receive an ETT through an elastic tubular member (such as, e.g., a tubular member made of latex, silicone; a tubular member coated or embedded with one or more of bacteriocidal agents, bacteriostatic agents, anesthetics, absorbing agents, and compounds inhibiting biofilm formation; etc.) that covers a balloon of the ETT and/or covers some portion of ETT distal and/or proximal sections; an anti-VAP system comprising an anti-VAP attachment that includes at least one port through which may be delivered antibacterial and/or anesthetic agents, and/or absorbing agents to the intubated patient; an anti-VAP system comprising an anti-VAP attachment that comprises a sleeve into which an ETT may be received, wherein a sleeved ETT fits through a patient's vocal cords and into the trachea and the sleeve spans the vocal cords; an anti-VAP system wherein an anti-VAP attachment is assembled onto an ETT. In another preferred embodiment, the invention provides a device or material that allows passage of a nasogastric tube (such as, e.g., a device that covers the nasogastric tube; an anti-VAP system that comprises an anti-VAP device or material that partially recedes into the upper esophagus; an anti-VAP system that comprises a device that is placeable as part of the nasogastric tube (such as, e.g., a device that is placeable after placement of the nasogastric tube; etc.); etc.

In another preferred embodiment, the invention provides a method of preventing ventilator associated pneumonia (VAP) in a patient (such as, e.g., a human patient, a veterinary patient) needing endotracheally intubation, comprising: disposing an anti-VAP device or an anti-VAP material in a region where secretions otherwise build up in the airway of the patient when intubated (such as, e.g., a disposing step that comprises attaching an anti-VAP attachment to an endotracheal tube; a disposing step that comprises placing an anti-VAP sponge or spongy material touching or near the ETT; a disposing step that comprises foaming an anti-VAP foamable material on or near the ETT; a disposing step that comprises providing an anti-VAP material (such as a gel, a powder, a liquid, etc.) on or near the ETT; etc.), including, e.g., methods wherein the disposing step is performed while the ETT is in the airway of the patient; methods wherein the disposing step is performed with the ETT outside the airway of the patient; prevention methods wherein the patient does not develop bacterial nosocomial pneumonia; prevention methods wherein the patient does not develop Gram positive, Gram negative or anaerobic VAP organisms; methods further including a step of providing airway anesthesia; In another preferred embodiment, the invention provides a device or material that allows passage of a nasogastric tube (such as, e.g., a device that covers the nasogastric tube; methods which use an anti-VAP device that allows passage of a nasogastric tube (such as an anti-VAP device that is placeable as part of the nasogastric tube; a device that is placeable after placement of the nasogastric tube; etc.); etc.

The invention in another preferred embodiment provides a method of reducing occurrence of ventilator associated pneumonia (VAP) in a population of patients endotracheally intubated, comprising: for each patient, disposing an anti-VAP device or an anti-VAP material in a region where secretions otherwise build up in the airway of the patient when intubated (such as disposing performed before patient intubation; disposing performed after patient intubation; disposing performed a mixture of before and after patient intubation), such as, e.g., methods comprising attaching an anti-VAP attachment to an endotracheal tube; methods wherein microaspiration is reduced; methods wherein oropharyngeal bacterial load is reduced; etc.

Another preferred embodiment of the invention provides a method of preventing ventilator associated pneumonia (VAP) in a patient (such as, e.g., a human patient, a veterinary patient) needing endotracheally intubation, comprising: disposing a space-occupying anti-VAP device or a space-occupying anti-VAP material in a mouth and/or oropharynx of a patient when intubated, wherein the anti-VAP device or anti-VAP material remains disposed therein during a period of intubation of the patient, and wherein the anti-VAP device or anti-VAP material is other than an endotracheal tube (ETT), such as methods in which silver embedded material (such as ribbons, pads, etc.) are disposed in an oropharynx of an ETT-intubated patient.

A further preferred embodiment of the invention provides a method of reducing or preventing colonization of the respiratory tract with gastrointestinal organisms, such as by, e.g., a device or material that partially recedes into the upper esophagus, whereby colonization of the respiratory tract with gastrointestinal organisms is reduced or prevented; etc.

In another preferred embodiment, the invention provides a method of preventing ventilator associated infection (such as, e.g., VAP) in a patient (such as, e.g., a human patient, a veterinary patient) needing intubation (such as, e.g., endotracheal intubation, nasogastric intubation), comprising: a) within an intubated patient, non-surgically disposing a controllably-removable space-occupying anti-infection device or a space-occupying anti-infection material in an open space where otherwise infection-causing organisms would accumulate, and wherein the anti-infection device or anti-infection material is other than an endotracheal tube (ETT) or a nasogastric tube; b) removing the anti-infection device or anti-infection material from the intubated patient. In such methods there may be further provided a step c) of subsequently re-occupying the open space where otherwise infection-causing organisms would accumulate in the intubated patient with an anti-infection device or anti-infection material.

The invention in a further preferred embodiment provides an anti-VAP system, comprising an anti-VAP device or an anti-VAP material, wherein the device or the material is sized and configured to be disposed in a patient airway intubated with a nasogastric tube.

Another preferred embodiment of the invention provides a method of reducing occurrence of ventilator associated pneumonia (VAP) in a patient whose esophagus is intubated with a nasogastric tube, comprising: disposing an anti-VAP device or an anti-VAP material in a region where secretions otherwise build up in the airway of the patient when intubated with the nasogastric tube and where these secretions may come from the esophagus.

The invention also provides in another preferred embodiment, a method of preventing VAP-causing oropharyngeal and tracheal secretions from traveling away from a first location in a patient to a second location where said secretions can cause VAP, comprising: disposing a barrier (such as, e.g., a barrier that has an absorbing capacity of at least 1 ml of secretions; a barrier that is a mouthpiece; etc.) in the patient, in a blocking position relative to the secretions in the first location, wherein the barrier is (1) an absorptive member and/or (2) a physical barrier; and physically blocking and/or absorbing the secretions from moving towards the second location in the patient, wherein the blocking and/or absorbing step is performed by the barrier, such as, e.g., inventive methods that include disposing a barrier that is a mouthpiece in a mouth of the patient and other inventive methods.

In another preferred embodiment, the invention provides a method of preventing VAP, comprising: disposing an absorptive mouthpiece in a mouth of a patient intubated with an ETT or a nasogastric tube.

The invention in another preferred embodiment provides an anti-VAP device, comprising: a mouthpiece having a hole therein and shaped to be received into a mouth of a patient, wherein the patient may be intubated with an ETT or nasogastric tube; wherein the hole in the mouthpiece is sized to accommodate an ETT or a nasogastric tube, such as, e.g., inventive anti-VAP devices wherein the mouthpiece comprises an absorbent material that absorbs VAP-causing secretions; and other inventive anti-VAP devices.

The invention also provides, in another preferred embodiment, a method of preventing VAP in a patient who is intubated with an ETT or a nasogastric tube, comprising: in a vicinity of the tube, installing a mechanical barrier to secretions, wherein the installed mechanical barrier has a secretions-accumulating capacity of at least 0.1 ml or 0.1 gm of secretions, the method including steps performed by the installed mechanical barrier of: receiving secretions from the patient without discharging any secretions back into the patient, and blocking secretions so that no secretions pass the mechanical barrier, such as, e.g., inventive methods that comprise installing a mechanical barrier that has a secretions-accumulating capacity of at least 1 ml or 1 gm of secretions; and other inventive methods.

The invention in another preferred embodiment provides an anti-VAP product for use in a patient who is intubated with an ETT or a nasogastric tube, comprising: a solid member that has a secretions-accumulating capacity of at least 0.1 ml or 0.1 gm of secretions, and that when installed in the patient in a vicinity of the tube, is a mechanical barrier that entirely blocks passage of secretions, such as, e.g., inventive products in which the solid member has a secretions-accumulating capacity of at least 1 ml or 1 gm of secretions; inventive products which are presaturated and/or resaturated with chlorhexidine, hydrogen peroxide, or other microbials or other medicinals for sustained contact and release to at least one dentition or mucosal surface; inventive products wherein the solid member is a one-size-fits-all shape installable in adult patients irrespective of tracheal diameter; inventive products wherein the solid member is a one-size-fits-all shape installable in pediatric patients irrespective of tracheal diameter; inventive products wherein the solid member is formed of an absorbent material and of a thickness for complete secretions-retention when installed in the patient, and at least a majority of secretions that enter the solid member are retained by the solid member while the solid member is installed in the patient; inventive products wherein the solid member retains all secretions that enter therein; and other inventive products.

The invention in a further preferred embodiment provides an oral hygiene method for a patient not intubated with an ETT or a nasogastric tube, comprising: disposing in the patient a mouthpiece device which is non-surgically removable, wherein the device comprises a solid member that has a secretions-accumulating capacity of at least 0.1 ml or 0.1 gm of secretions, and maintaining oral hygiene and reducing an oropharyngeal bacterial burden that would be associated with aspiration pneumonia, performed by the disposed device, such as, e.g., inventive methods wherein the mouthpiece device-disposing is an alternative to traditional oral hygiene including tooth brushing, flossing and antiseptic mouth rinses; inventive methods that include saturating and/or resaturating the mouthpiece device with medicinals; and other inventive methods.

In another preferred embodiment, the invention provides a method of preventing VAP in a patient intubated with an endotracheal tube or a nasogastric tube, comprising: disposing in the patient a device that is not the tube or any part of the tube, wherein the disposed device is macroscopic-sized and participates in, and/or contributes to, preventing VAP, such as, e.g., prevention methods that include, after the disposed device has remained in the intubated patient for a period of time, non-surgically removing the disposed device from the patient.

BRIEF SUMMARY OF THE DRAWINGS

FIG. 2 shows a traditional endotracheal tube ETT with a pilot balloon for cuff inflation. The tube ETT is shown in relation to the supraglottic space 203, the distal trachea 205, and the subglottic space 200.

FIG. 18A shows a thinned sample (left) 1801 next to a hydrated thinned sample (right) 1802.

DETAILED DESCRIPTION OF A PREFERRED EMBODIMENT OF THE INVENTION

Figure 1:
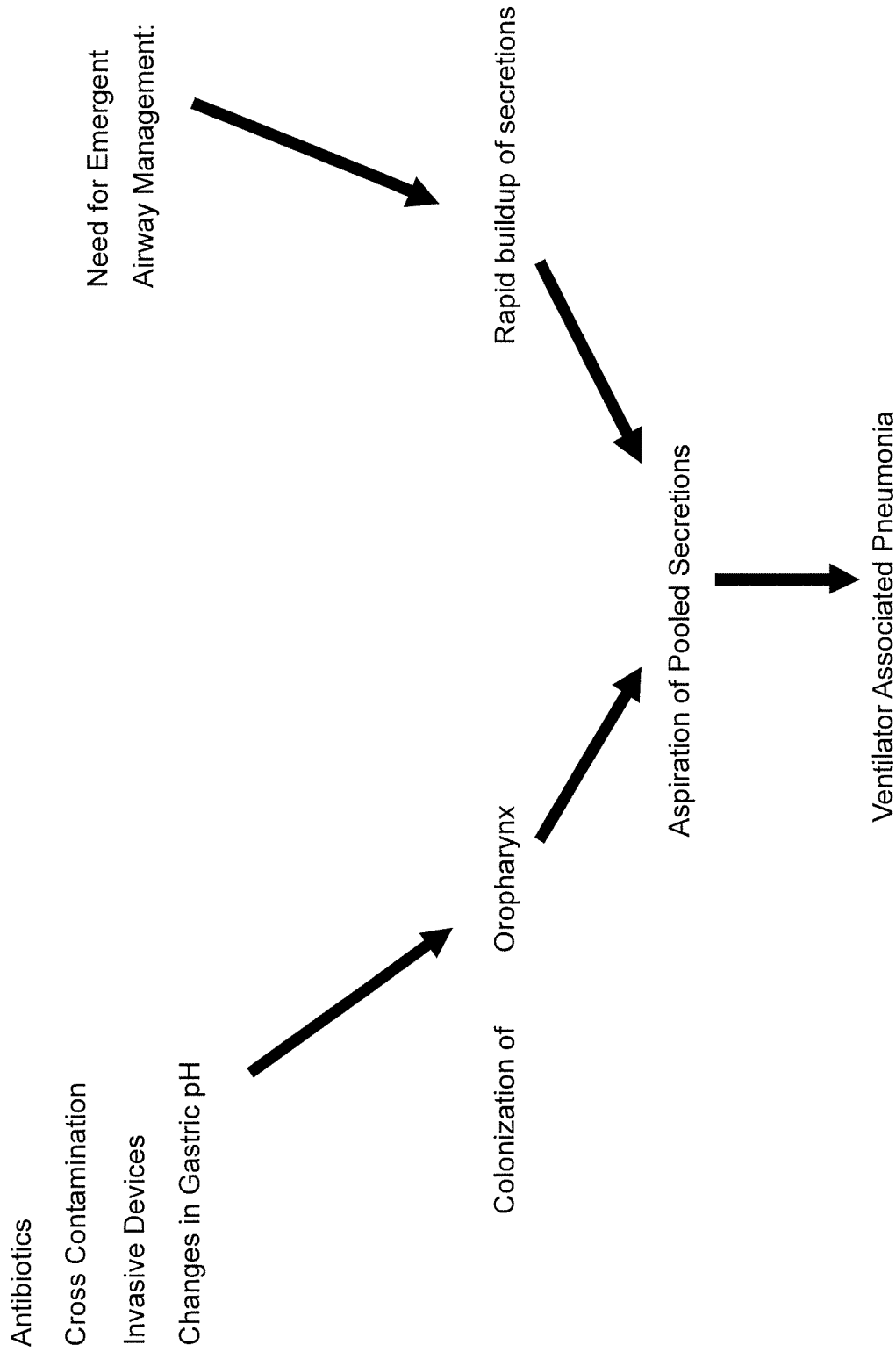
FIG. 1 is a chart showing a common pathway to development of VAP both early and late after intubation of a patient. The present invention is useful in both situations to reduce VAP.
Figure 2:
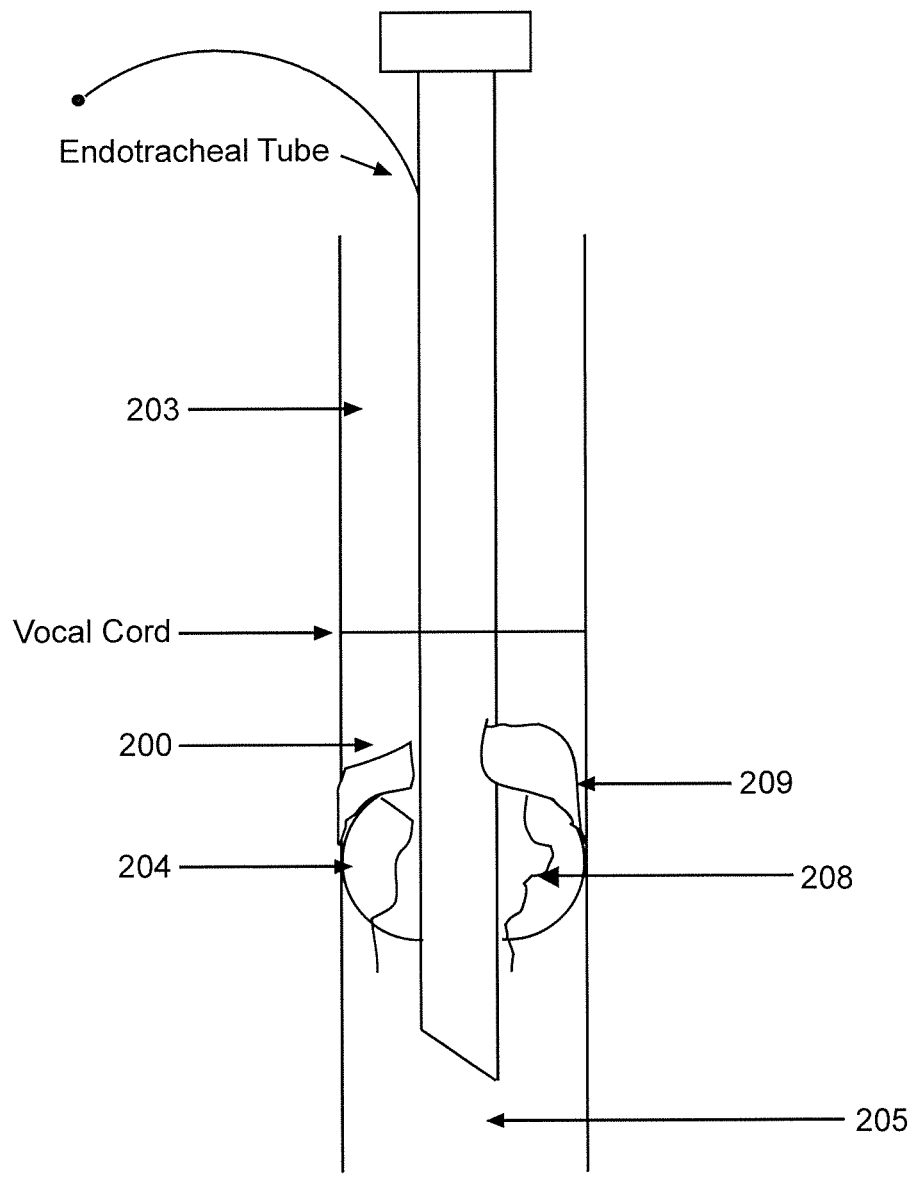
FIG. 2 is a cross-sectional view of pooled secretions in the subglottic space 200 (i.e., the space between inflated endotracheal balloon and vocal cords VC), which represents the problem when the invention is not in use.

The invention provides anti-VAP activity by controlling the space (namely, at and/or near (such as within about 1 cm of) the ETT of an intubated patient, such as space 208 in FIG. 2) where, if uncontrolled, VAP-causing agents otherwise accumulate and proceed to cause VAP. The accumulation of such secretions may be appreciated by referring to FIG. 2, which depicts (when the invention is not in use) pooled secretions in the subglottic space 200 (the space between the inflated endotracheal balloon and the vocal cords VC). This pooling results in microaspiration around the inflated endotracheal tube cuff 204 through small channels created between the cuff 204 and tracheal mucosa. Leakage 208 occurs of subglottic secretions through channels created from incomplete ETT balloon inflation. Such leakage 208 leads to VAP, as the present inventors have recognized.

In the invention, the space at and/or near the ETT (such as the space 209 of accumulating subglottic secretions in FIG. 2) is subjected to affirmative anti-VAP control, such as by occupying the space (such as by an anti-VAP device or an anti-VAP material (such as, e.g., a foam, liquid, gel, sponge, hydrogel, biomaterial, etc.)). For example, a space-occupying anti-VAP material or anti-VAP device is caused to occupy the space at and/or near the ETT, and the space-occupying material or device after a time is further controlled (such as by removing such a space-occupying anti-VAP material or anti-VAP device after a time). Subsequently, the space may be further controlled, such as by again causing the space to be re-occupied with an anti-VAP space-occupying material or device (which is not required to be the same as the removed anti-VAP material or device).

An anti-VAP material or anti-VAP device is not necessarily required to be treated or coated or to include an organism-killing agent. An anti-VAP material or anti-VAP device may, for example, merely provide a site for VAP-causing organisms to accumulate, with the site being removable from the patient before the accumulated VAP-causing organisms can cause VAP.

Examples of anti-VAP devices that may be used in an anti-VAP system include, e.g., attachments or adjuncts that can be added to any endotracheal tube before and in some cases after intubation, such as an anti-VAP device that is a sleeve. An anti-VAP device that is an attachment to an ETT advantageously removes problems of switching to a specific new endotracheal tube, and further increases the potential to reduce VAP by multiple and combined means, again without relying on the specifics of the underlying endotracheal tube used. An anti-VAP attachment to an ETT also advantageously allows for more flexibility as new materials and methods evolve in airway management including the prevention of VAP. An anti-VAP device may be disposable or may be reusable after treatment (such as sterilizing treatment).

An example of an anti-VAP device is a disposable sleeve. The disposable sleeve may be provided to surround the endotracheal tube balloon and/or more proximal sections of the tube.

Another example of an anti-VAP device is an elastic tubular member. When using the inventive elastic tubular member, there also may be practiced conventional strategies to reduce the potential for small longitudinal folds to occur upon endotracheal tube cuff inflation, such as, e.g., constructing the ETT balloon with other materials such as latex or silicone to reduce the formation of these channels or by eliminating the balloon altogether and replacing it with "gills". However, advantageously, the inventive elastic tubular member can be used with various endotracheal tubes and thereby the invention advantageously provides practical flexibility. An ETT may be placed through an inventive elastic tubular member that covers the native balloon and some portion of the distal and proximal ETT. This inventive tubular member could be made, e.g., of latex, silicone or other materials, which are coated or embedded with sliver or other bacteriocidal/static agents as well as anesthetics. These materials might be made in a manner or contain compounds inhibiting the formation of biofilms. The materials from which to form the inventive tubular members may be made to display various innate or induced electrostatic charges, which have been demonstrated to favorably affect inflammation and bacterial growth. The materials from which to form the inventive tubular members could allow for exogenous delivery (through ports in the sleeve) of antibacterial or anesthetic agents.

Anti-VAP devices and anti-VAP materials are not necessarily exclusive of each other. For example, an anti-VAP material may be formed into or used with an anti-VAP device. Importantly, the present invention is not limited to solids and non-solids may be used in practicing the inventive control of space where VAP-causing organisms otherwise accumulate. "Material" broadly includes any form, such as solids, liquids, foams, hydrogels, semi-solids, etc.

According to the invention, preferably a physical barrier (most preferably, an absorbent physical barrier that absorbs the secretions) is established where secretions (such as VAP-causing secretions) will encounter the physical barrier and be prevented by the physical barrier from moving from one location (such as, e.g., in a subglottic space, in the oropharynx, etc.) to another location elsewhere in the patient where their presence is likely to be even more problematic. The invention provides, for example, capture of VAP-causing secretions within a patient where an absorbent material disposed within the patient captures the secretions, after which the absorbent material removed after having spent time (such as a time on the order of about an hour, a time on the order of about two hours, etc.) in the patient absorbing secretions. For example, an inventive mouthpiece comprising an absorbent material is inserted in a patient's mouth and left inserted for a time during which the mouthpiece acts as a physical barrier encountered by the secretions and absorbs secretions (such as, e.g., at least 0.1 ml of secretions, preferably at least 1 ml of secretions), after which the used mouthpiece, that contains the captured secretions, is removed by medical personnel from the patient's mouth.

Example 1 (Leakage Experiment)

Experimentation regarding anti-VAP devices and/or anti-VAP materials was performed as follows.

7 mm ETT inflated in the barrel of 20 cc syringe, with dye leaking occurring around the cuff through channels formed between the cuff and the balloon: A photograph was taken that shows a screening methodology reported in other studies that uses the barrel of a 20 cc syringe to act as the trachea. It is intubated with an endotracheal tube followed by inflation of the cuff and introduction of dye above the balloon. A 7 mm ETT was used. Leakage of dye around the balloon can then be observed for. Leakage of dye is seen when the balloon is filled with 10 cc air.

7 mm ETT with rubber latex cover around the balloon, according to an embodiment of the invention; native balloon inflated: In another photograph, another 7 mm ETT is used but before insertion into the "trachea" it was placed through a simple piece of a latex rubber drain. Inflation of the native balloon followed by instillation of dye was then performed. There is no evidence of leakage, even with manipulation of the proximal ETT. Identical results have been found using the finger portion of simple latex gloves. The tubular member may be constructed in such a manner that it comes with its own inflation port. Sleeves may be made with portions of the sleeve (which surround the ETT native balloon) expanding as the native balloon is inflated or these sleeves could contain their own balloon and inflation mechanisms. Inflation mechanisms may include, e.g., filling the sleeve balloon with self-expanding foam similar to that of the Bivona foam cuff product line. Again the sleeves may be coated with various materials or could have channels and ports allowing the delivery of various beneficial agents.

Example 2

Figure 3:
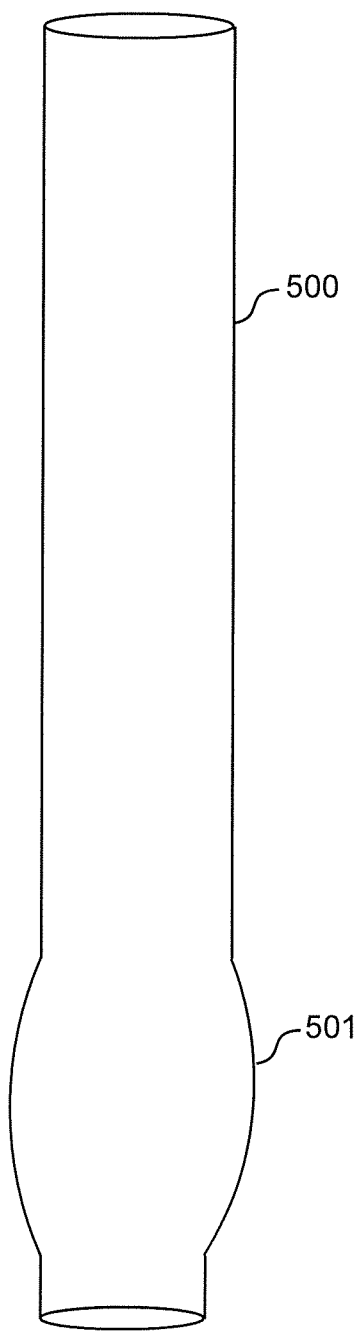
FIGS. 3 and 4 are cross-sectional views of an inventive open-ended sleeve through which an ETT is placed.

FIG. 3 shows an inventive open ended sleeve 500 or condom to be placed over an ETT prior to intubation. A portion 501 of the sleeve 500 goes over the ETT balloon and expands as the balloon expands.

Modification of the end of the sleeve 500 allows for the native balloon to be covered with a material that would not lead to formation of channels between the ETT attachment and the tracheal mucosa when the native balloon is inflated. The sleeve 500 may be embedded with antimicrobials/bacteriostatic agents and anaesthetics. Materials used for forming the sleeve 500 preferably are resistant to formation of biofilms.

Figure 4:
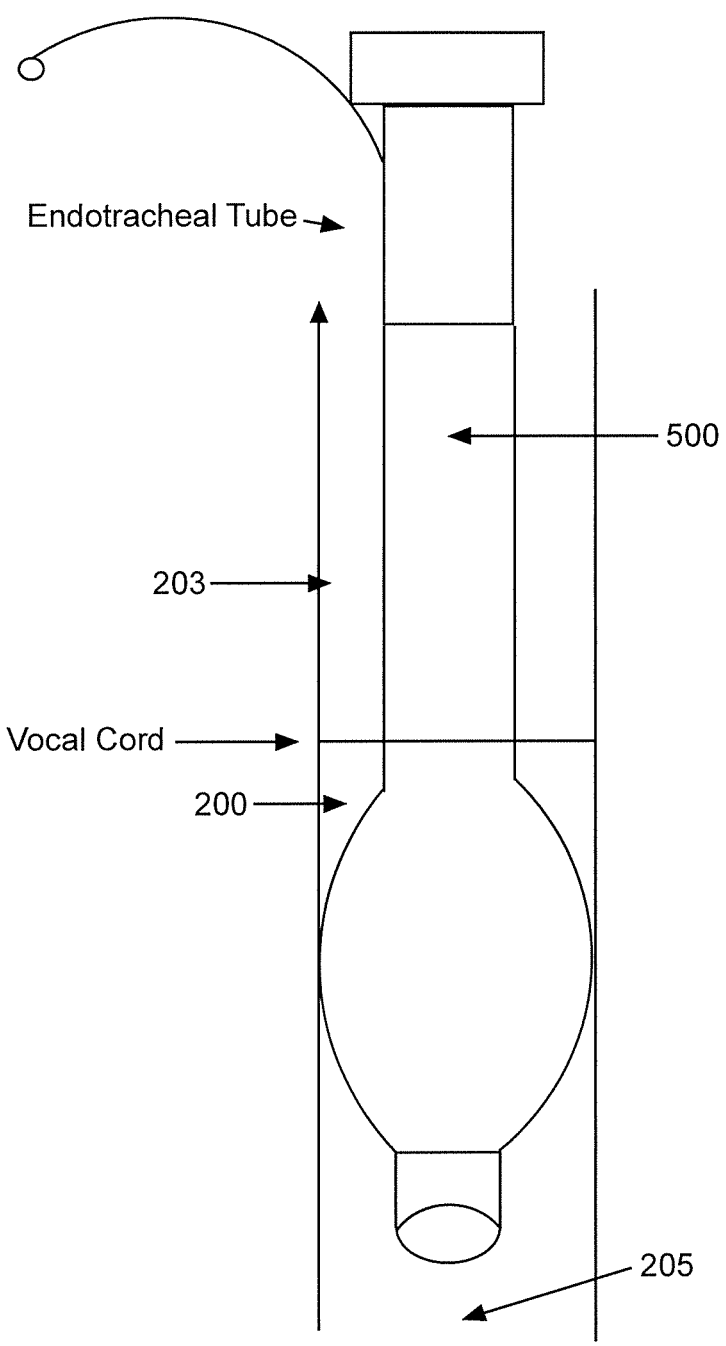

FIG. 4 shows the inventive sleeve 500 extending from below the balloon to the proximal tube when the sleeve 500 is used with a traditional endotracheal tube ETT with a pilot balloon for cuff inflation. The endotracheal tube ETT, supraglottic space 203, vocal cords VC, and subglottic space 200 in FIG. 4 are as in FIG. 2. The sleeve 500 optionally may have a separate inflation port (not shown) for the balloon cover portion.

Example 2A

Figure 5:
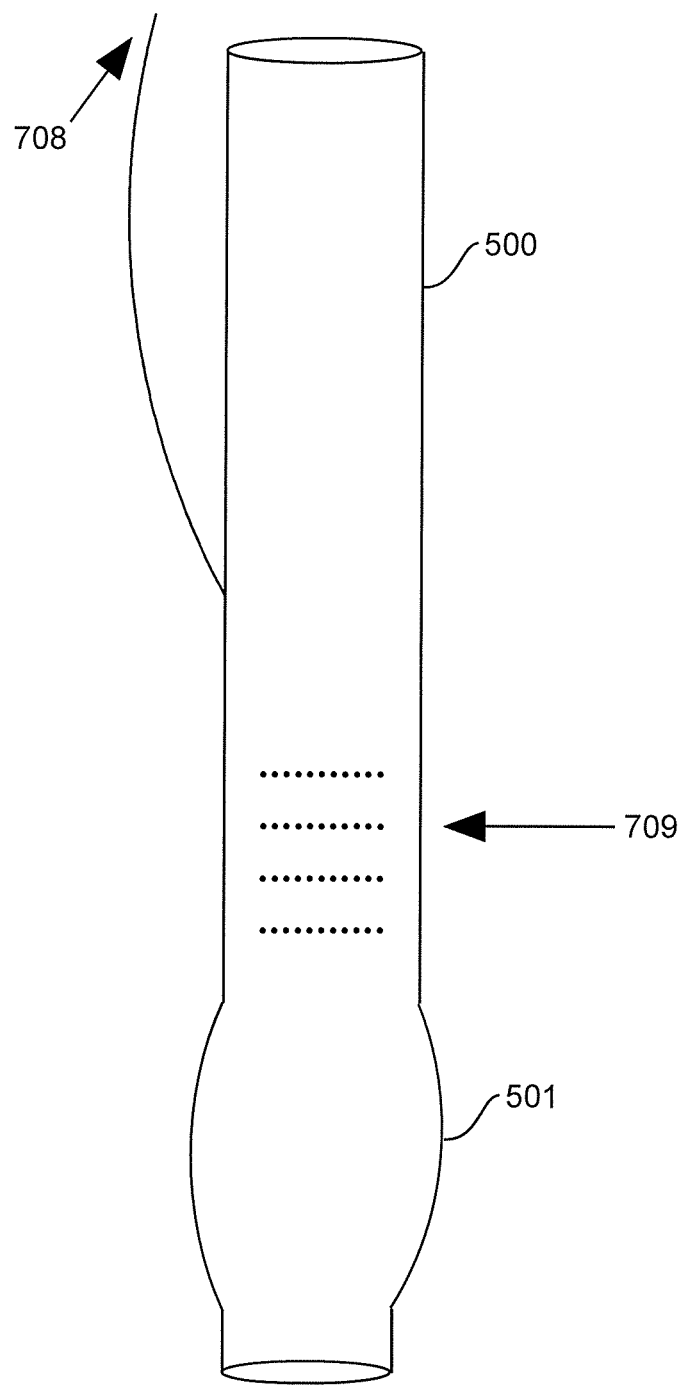
FIG. 5 is a cross-sectional view of the sleeve of FIG. 3 modified to include ports for delivery of compounds such as antimicrobials and anesthetics.

FIG. 5 is a modified version of the sleeve 500 of FIG. 3, modified to include ports 709 for delivery of compounds (such as antimicrobials, anesthetics, etc.) and port 708 for injection of compounds (such as anesthetics, antimicrobials, etc.).

Example 2B

Figure 7:
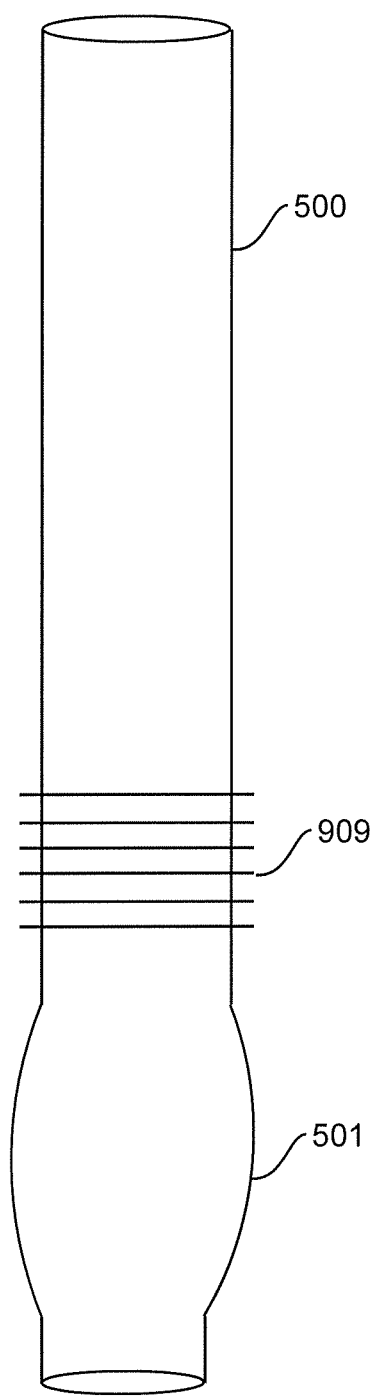
FIG. 7 shows an inventive sleeve in which conventional barrier strategies such as gills additionally may be used.

The inventive sleeves may have a conventional barrier technology such as "gills" (e.g., Reali-Forster et al, supra) attached to them. For example, a sleeve 500 (of FIG. 3) may have gills 909 added as shown in FIG. 7, to increase the barrier function of the sleeve 500.

Example 3

Figure 6:
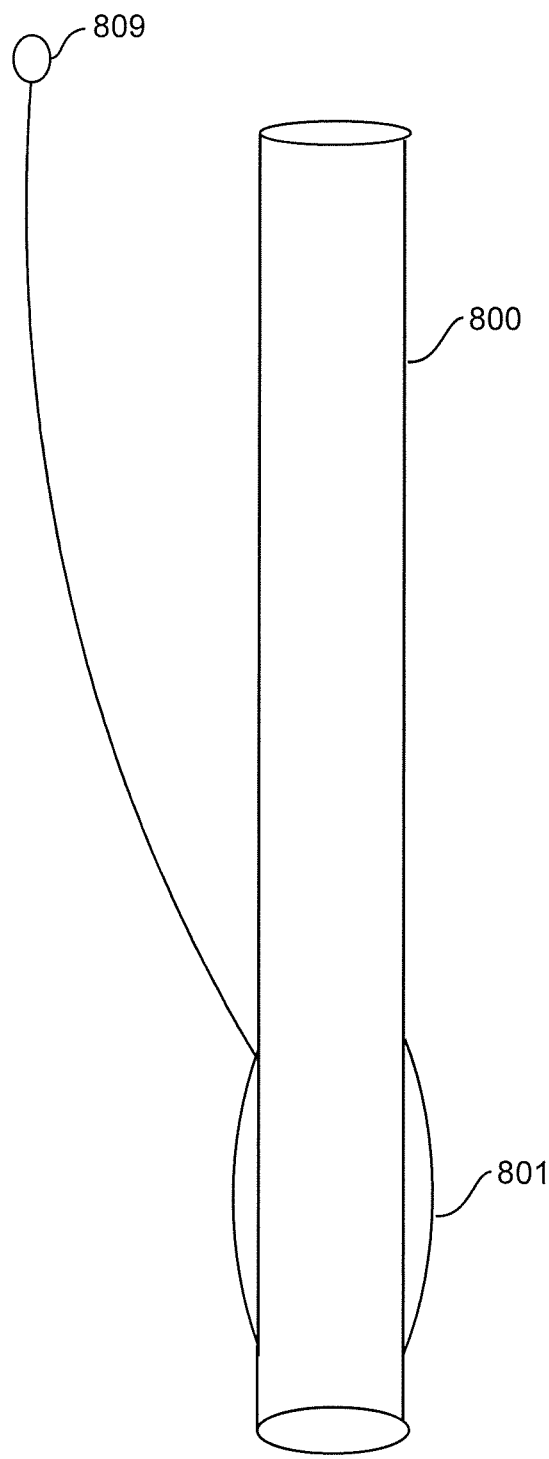
FIG. 6 shows an inventive sleeve containing its own balloon and inflation mechanisms.

Referring to FIG. 6, the inventive sleeve 800 (which may contain special compounds) contains its own balloon 801 (which may be made of, e.g., silicone, latex, or other material resistant to the formation of channels) and inflation mechanisms. The open-ended sleeve 800 or condom is placed over the ETT prior to intubation. The sleeve 800 contains its own balloon 801 expanded with air or containing foam which self-expands. Pilot balloon and stem 809 for inflation of the sleeve balloon are shown in FIG. 6. The sleeve balloon 801 also may contain foam sponge similar to Bivona strategy and foam sponge deflated by aspiration, and then inflated when exposed to atmospheric pressure. The stem 809 is then attached in line to a ventilator circuit. That is, the ports of the balloons 801 are hooked in line with the ventilator circuit so that additional expansion takes place during mechanical ventilation. The balloons 801 may be coated with antimicrobials and anesthetics.

Example 4

An anti-VAP attachments may include, e.g., a sleeve containing a suction and/or delivery port so that subglottic secretions could be suctioned. Alternatively, the subglottic space could be obliterated by injecting various water-soluble hydrogels or foaming agents containing bacteriostatic and anesthetic properties to act as a barrier and to bathe the mucosa and vocal cords. This could be exchanged daily by suctioning and then injecting new material. Agents conventionally used for wound care may be applied.

Figure 8:
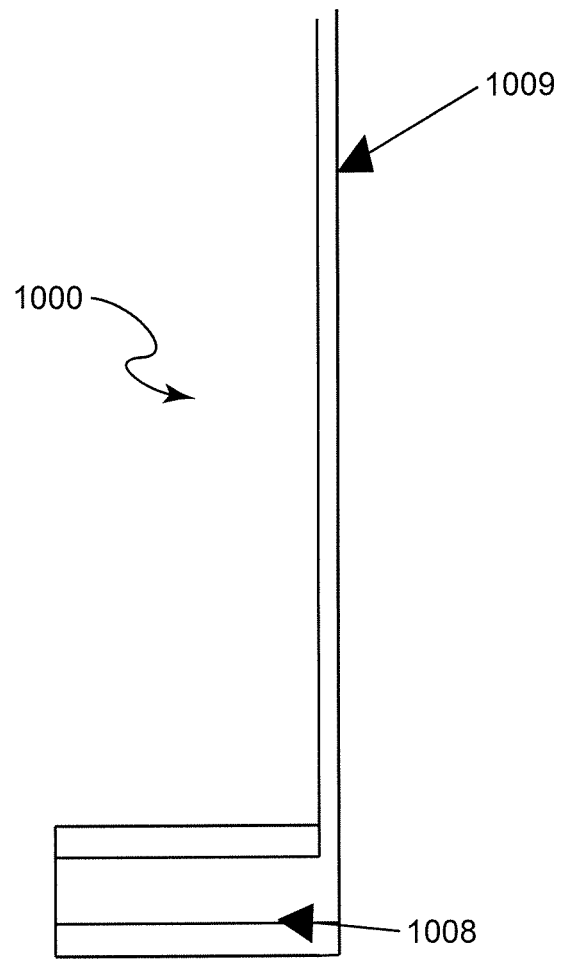
FIGS. 8 and 9 are views of an inventive anti-VAP attachment that allows for suctioning of the subglottic space or delivery of hydrogels or other compounds to the subglottic space to obliterate the space and act as an additional barrier.

In FIG. 8, a suctioning ring attachment 1000 is shown, that may be placed around an ETT either before or after patient intubation. Port 1009 in FIG. 8 is a suctioning port or delivery port. The inventive sleeve in FIG. 8 includes a near circumferential opening 1008 of the ring connecting to the port 1009 for suctioning or delivery of hydrogel barrier or other materials.

Example 4A

Figure 9:
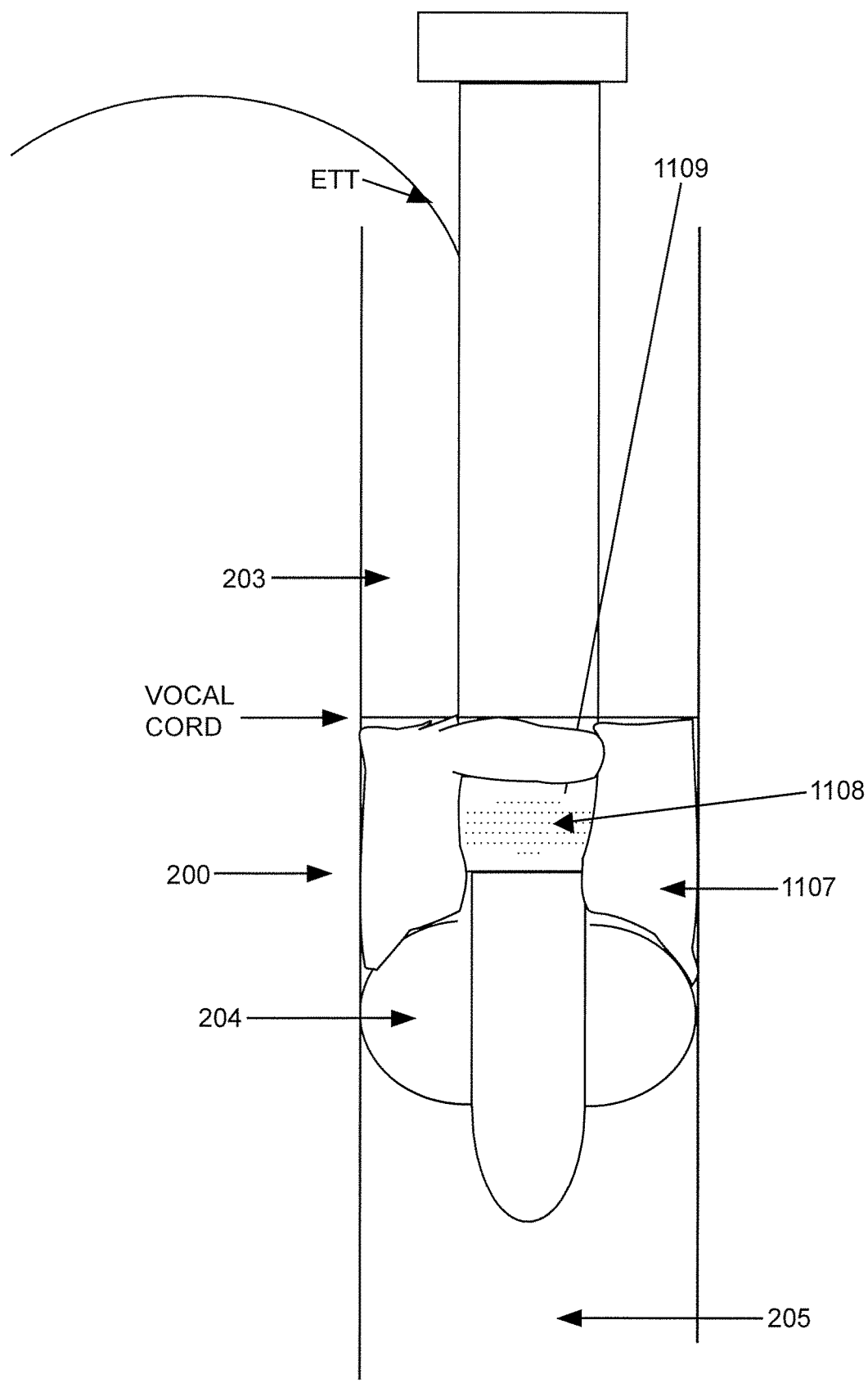

FIG. 9 shows another inventive port-containing sleeve, shown after intubation of the ETT. As in earlier figures, the following are comparably numbered: the endotracheal tube ETT which may be a traditional endotracheal tube, the supraglottic space 203, the vocal cords VC, the subglottic space 200, the inflated endotracheal tube cuff 204 and distal trachea 205.

In FIG. 9, sleeve port 1109 is for injection of additional hydrogel to fill both supraglottic and subglottic space. The port 1109 may also contain conductive materials to produce various charges around the sleeve.

The ETT sleeve has ports 1108 to allow for extrusion of hydrogel into the supraglottic space 203 and subglottic space 200. Injected hydrogel (or other material) 1107 obliterates subglottic space 200 providing a barrier function and delivery of antimicrobial, anesthetic, and other compounds.

Example 5

Figure 10:
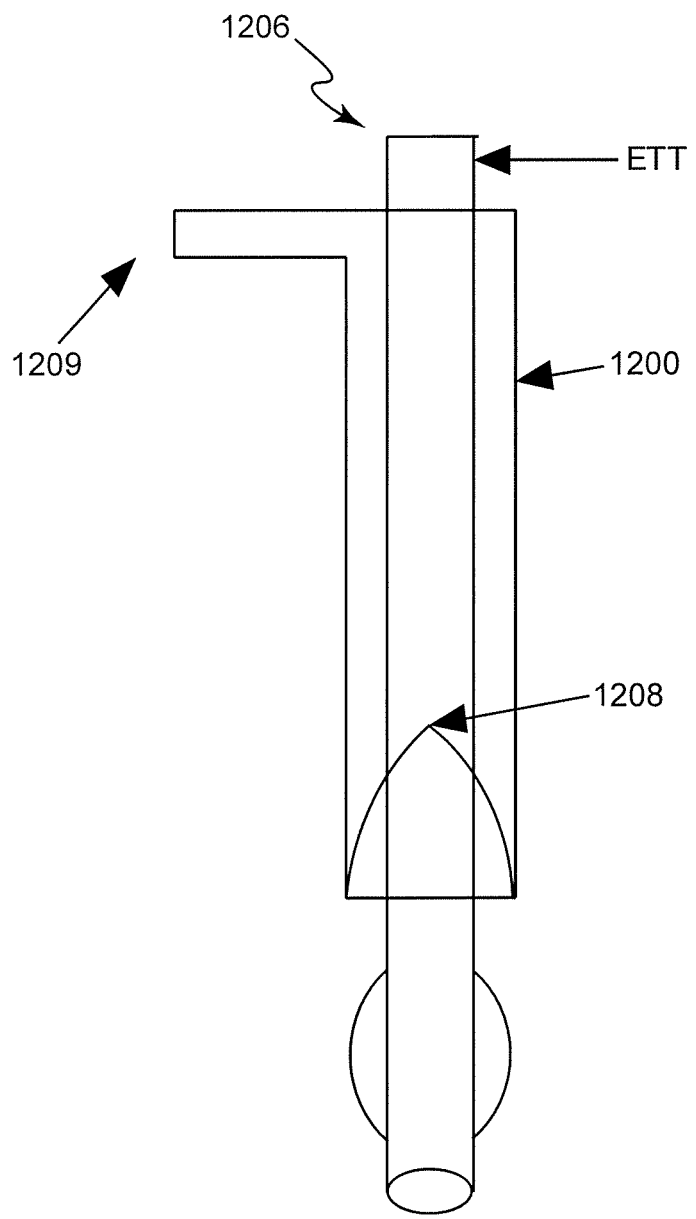
FIG. 10 shows an inventive sleeve ETT attachment that isolates the supraglottic area preventing passage of secretions to the subglottic space.

As seen with reference to FIG. 10, another example of an inventive anti-VAP attachment to a tube ETT is a sleeve 1200 allowing isolation of the supraglottic area similar to that of the laryngeal mask airway. The device of FIG. 10 includes a flexible covering 1206 allowing delivery of aerosolized or other forms of anesthetics or antimicrobials to the supra and sublottic areas. Optionally, the device may be modified to allow for suction and could be formed to fit over or surround the epiglottis similar to a laryngeal mask airway.

Sleeve part 1208 is a covering that may fit over the epiglottis/supraglottic area similar to a laryngeal mask airway. Optionally an inflatable balloon may be used to make the seal around the supraglottic area.

The sleeve 1200 may contain antimicrobials and anesthetics. Suctioning may take place through this anti-VAP device. In addition, this anti-VAP device may allow for delivery of agents to the supra and immediate subglottic area such as anesthetic or antibacterial aerosols. Port 1209 is for introduction of compounds (such as aerosolized compounds, antimicrobials, anesethetics, etc.) to the supraglottic and subglottic space, or suctioning.

Again, as mentioned for other anti-VAP sleeves, this anti-VAP sleeve may be coated with or contain antimicrobials, bacteriocidal and anesthetic agents, etc.

An example of a prototype that was made and photographed is a thinned product bent into an inventive circular sleeve with the ends sutured together. Then the inventive sleeve was placed over an endotracheal tube.

Example 6

The invention also provides anti-VAP foam/sponge sleeves (such as wound foams/sponges which contain dyes and other material which can be bacteriostatic) that may be attached and then activated causing them to swell to obliterate the subglottic space. The foam absorbs secretions and increases contact time of bacteria with a bactericidal agent used in or with the foam. The foam may traverse the vocal cords.

Referring to FIGS. 11-14, ETT attachments (such as the foam/hydrogel sleeve 1300 in FIG. 11) which may be made of foam are shown. Foam ETT attachments expand when placed into contact with moisture. The foam may be embedded with antimicrobials or anesthetics. The sleeves shown in FIGS. 11-14 show a strategy in which a barrier function and drug delivery are provided.

Figure 11:
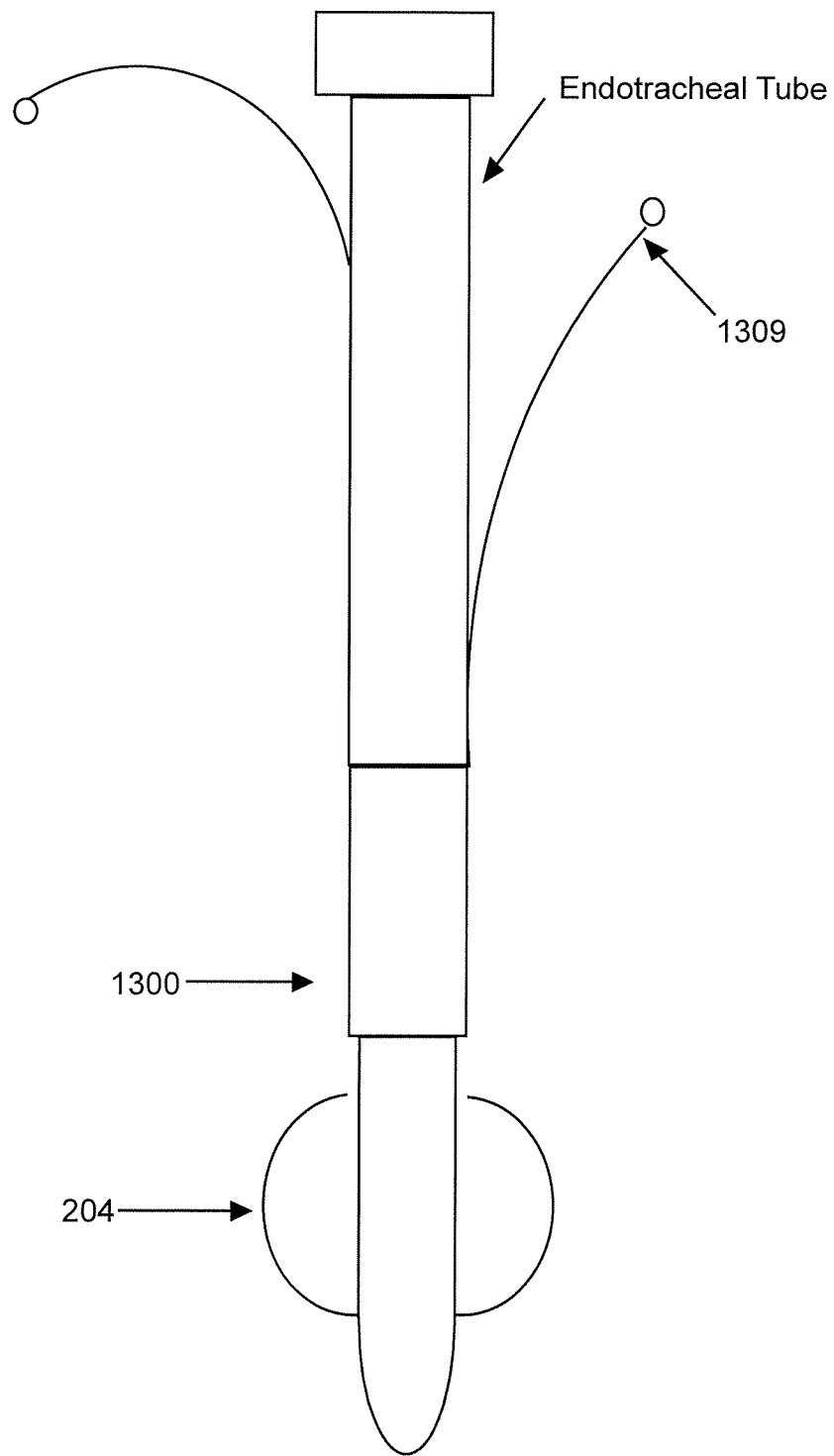
FIGS. 11-14 show inventive anti-VAP foam ETT attachments.

In FIG. 11, an endotracheal tube ETT wearing a foam/hydrogel sleeve 1300 is shown prior to intubation. Through a hydrogel sleeve port 1309, there may be injected water, additional hydrogel, or other activating agents. FIG. 11 shows a non-hydrated status of the sleeve 1300.

Figure 12:
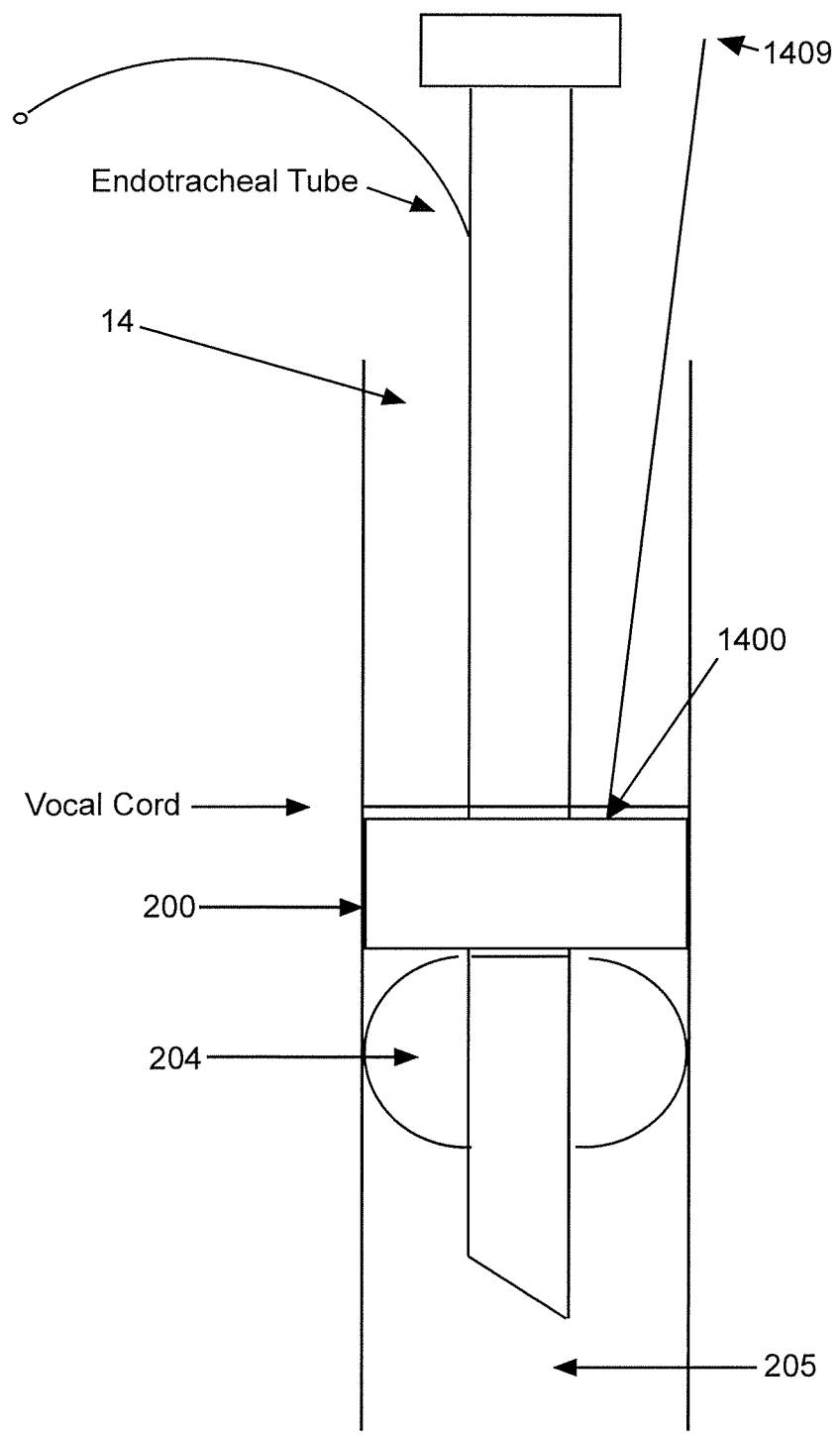

In FIG. 12, a medical foam material sleeve 1400 assembled on an ETT is activated to an expanded state below the trachea 14. A stem 1409 is provided to the sleeve 1400 allowing hydration.

Figure 13:
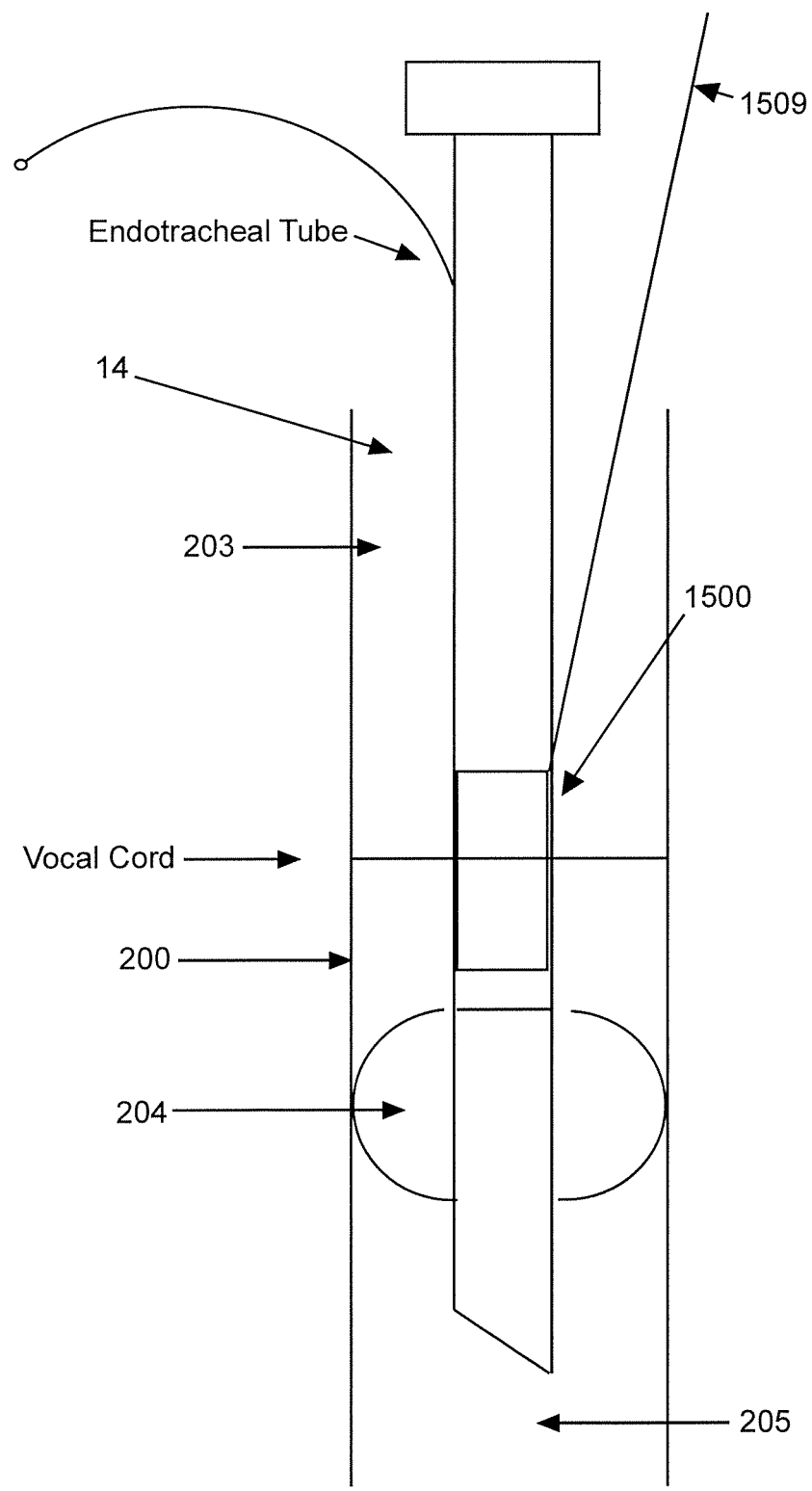

In FIG. 13, a sleeve 1500 (such as a sleeve comprising hydrogel, non-hydrated medical foam, or another material) is assembled on an ETT, in an unactivated state, and spanning the vocal cords VC. A stem 1509 to the sleeve 1500 permits hydration.

Figure 14:
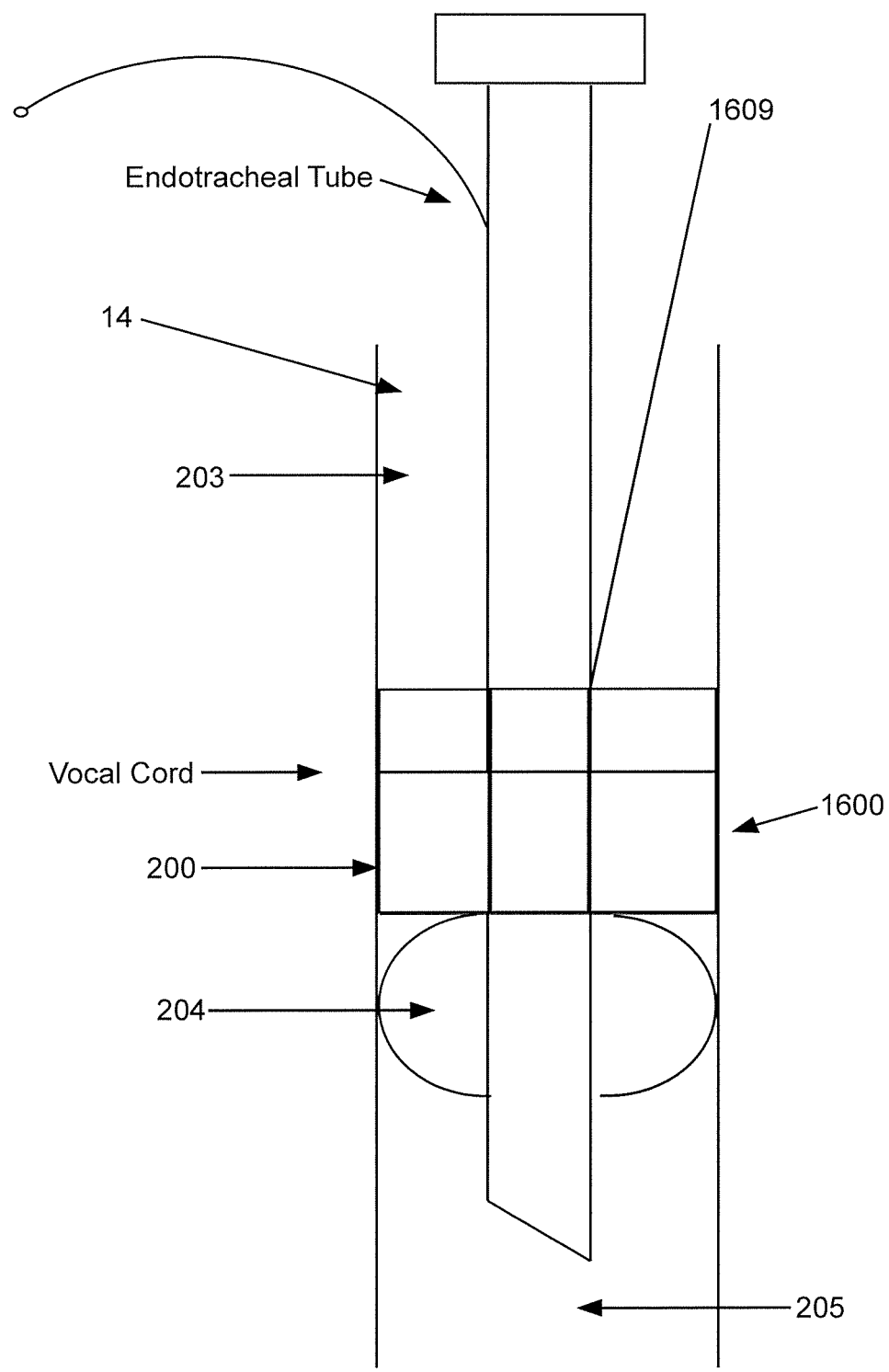
Figure 16:
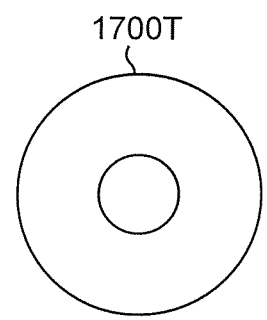
FIGS. 16 and 17 show respective top view 1700T and side view 1700S of ball 1700 of FIG. 15.
Figure 17:
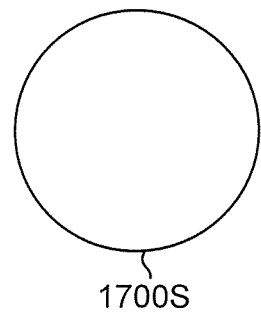

In FIG. 14, an activated sleeve 1600 (such as a hydrogel sleeve) is shown spanning the vocal cords VC, and expanding to consume most of the subglottic space forming an impenetrable barrier. A stem 1609 to the sleeve 1600 permits hydration. The hydrate foam or other material of the sleeve 1600 spans through the vocal cords VC essentially eliminating the subglottic space.

Example 7

A foam/sponge ball or other shaped member (sleeve) with a hollow core may be placed around the ETT. This ball or sponge sleeve may be gently compressed and slid far down into the supraglottic area of the oropharynx where it acts act as a super absorber of secretions. The foam may be embedded with antimicrobials of various sorts and optionally may contain and anesthetic. It may be nonadherent and thus friendly to the epiglottis. The foam ball, sleeve, or ring may be replaced at regular intervals.

Figure 15:
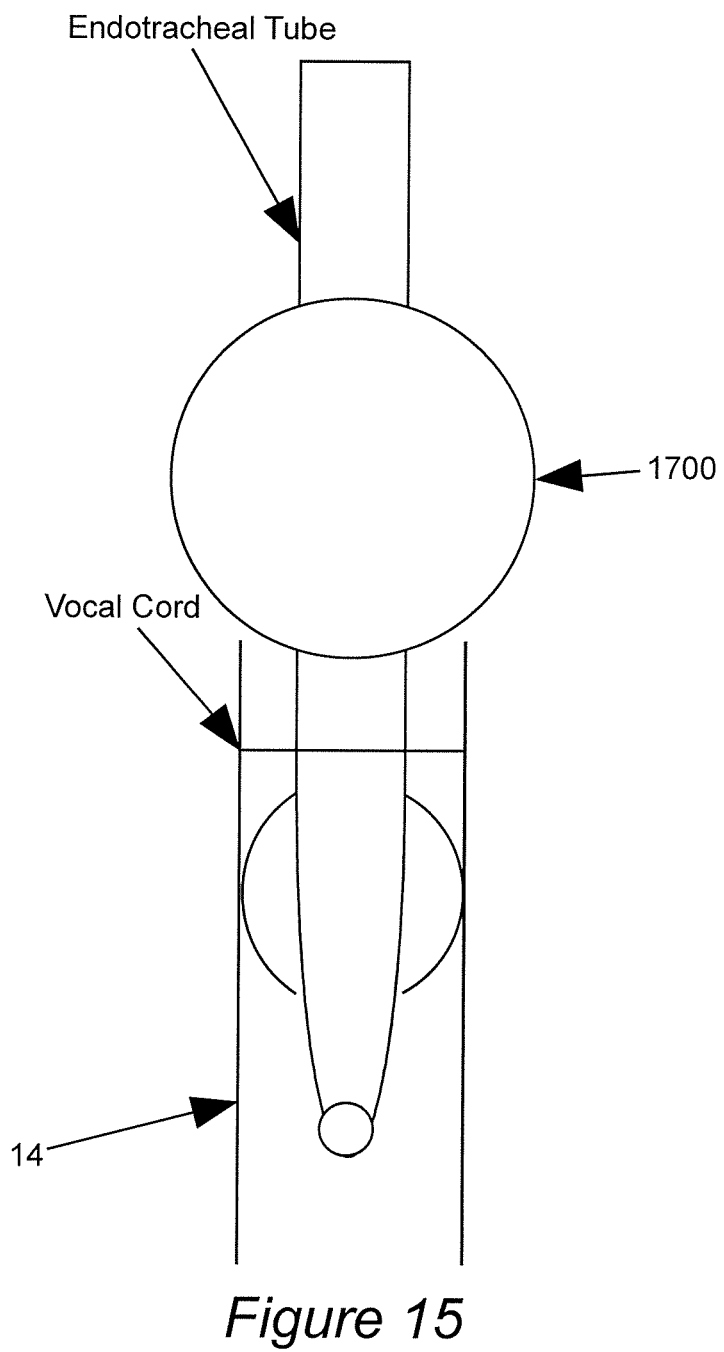
FIG. 15 shows an inventive anti-VAP system using a foam or sponge ball.
Figure 18:
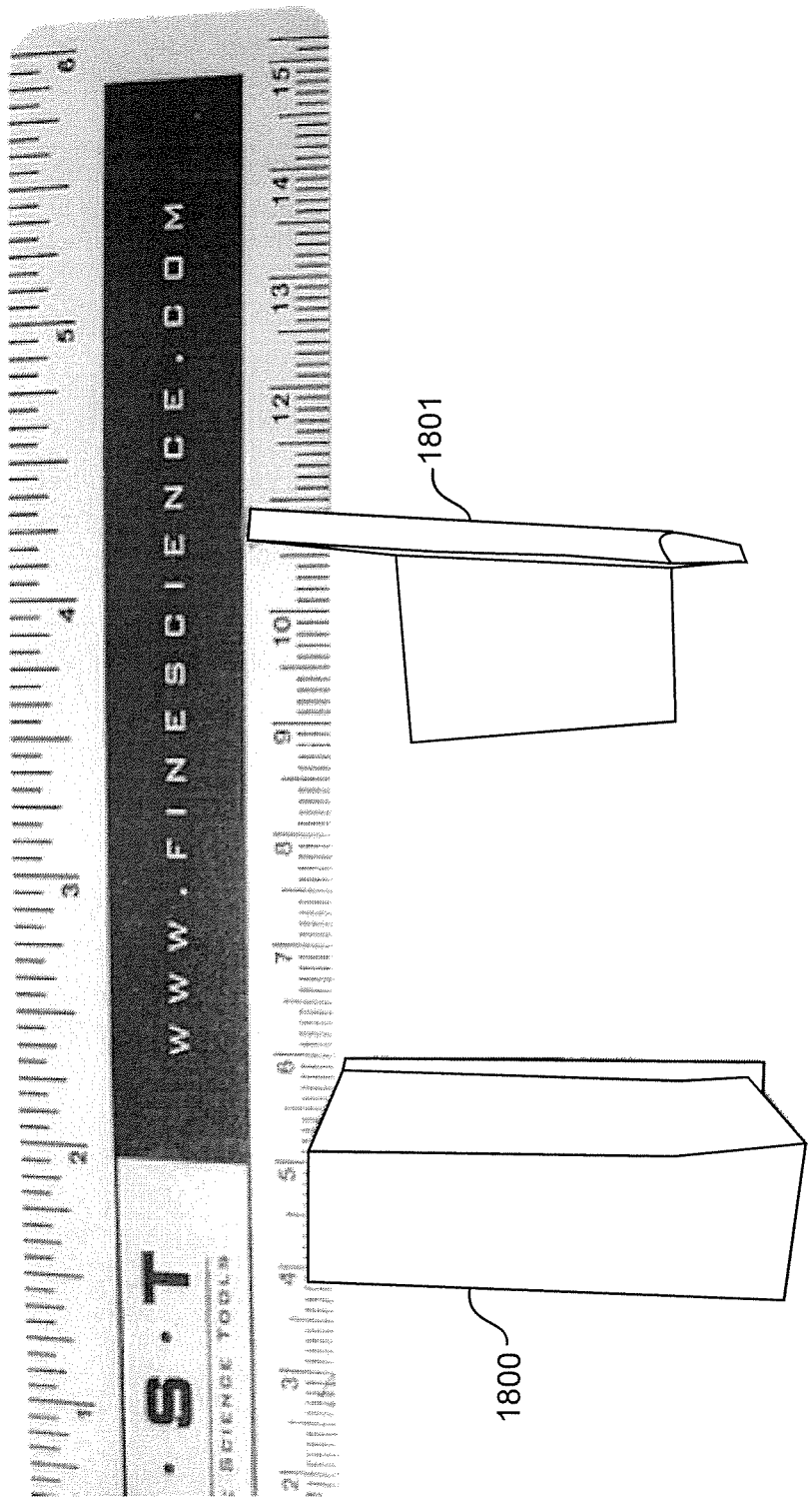
FIG. 18 shows a non-hydrated sample (left) 1800 next to a thinned sample (right) 1801.
Figure 18B:
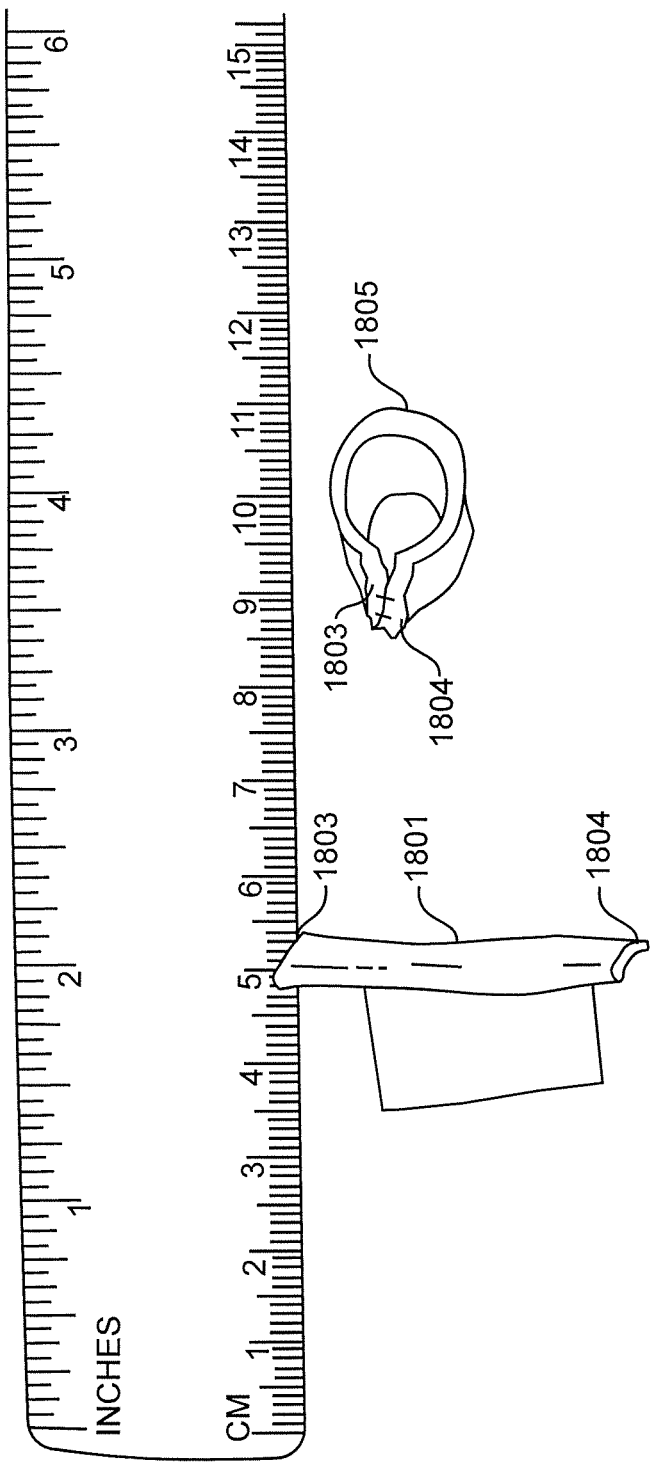
FIG. 18B shows a thinned product (left) 1801 with ends 1803, 1804 bent into an inventive circular sleeve (right) 1805 with the ends 1803, 1804 sutured together.
Figure 18C:
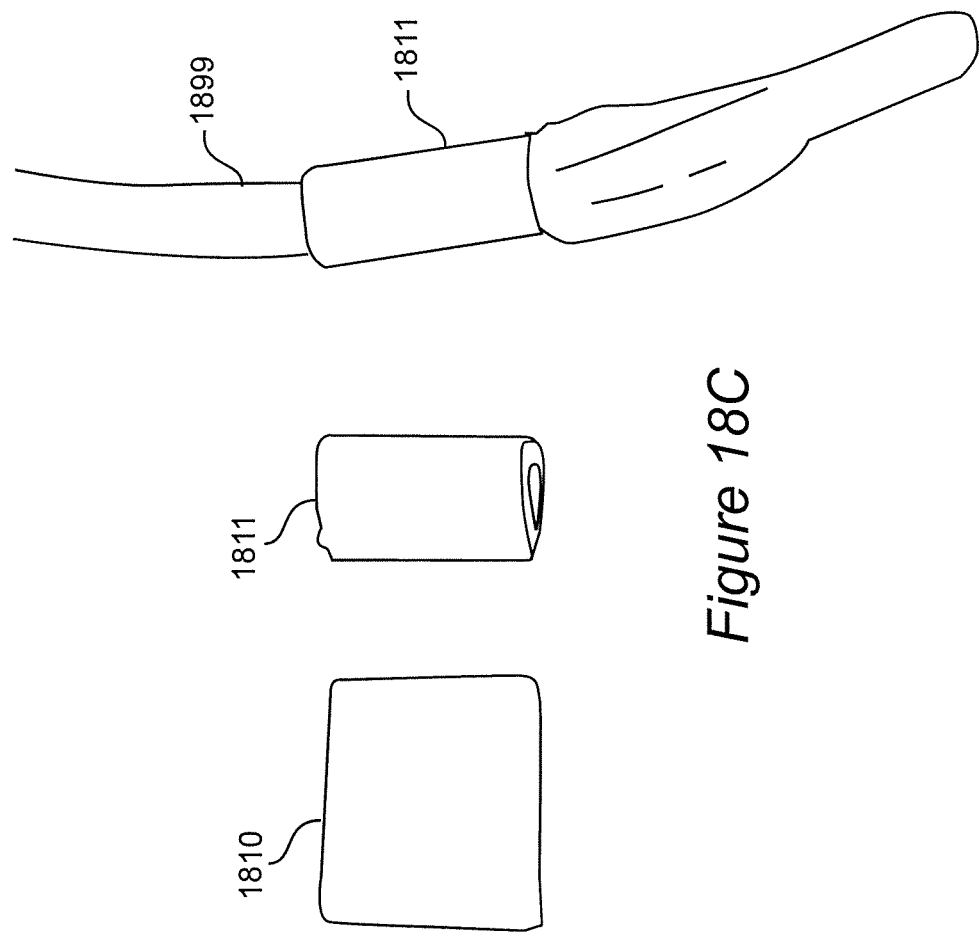
FIG. 18C shows a thinned sample (left) 1810 made into an inventive sleeve (middle) 1811, with the inventive sleeve 1811 placed over an endotracheal tube (right) 1899.

Referring to FIG. 15, a foam/sponge ball 1700 is shown, but alternately a non-ball shape may be used, preferably a shape that conforms to the entire posterior pharynx. Ball 1700T is the top view and ball 1700S is the side view of the oropharyngeal foam ball 1700. The ball 1700 acts as a secretion barrier and absorbs secretions. The ball 1700 may be loaded with anesthetics and/or antimicrobials/bacteriostatic agents. The ball 1700 is removable and replaceable.

Example 8

The invention may be applied to nasogastric tubes (esophageal and oropharyngeal portions), to reduce aerodigestive colonization to which nasogastric tubes otherwise contribute. Anti-infection devices and anti-infection materials (such as, e.g., removable, disposable anti-infection devices and anti-infection materials) may be used to control the space within a patient intubated with a nasogastric tube in the space where otherwise infection-causing organisms would accumulate.

The inventive devices, materials, systems and methods discussed herein with references to the figures are especially preferred for use with human patients but also are useful in veterinary embodiments. In an example of using the invention during intubation, by comparison to a standard endotracheal tube that passes through the vocal cords, an inventive non-hydrated sleeved endotracheal tube passes through the vocal cords and into the trachea, with the sleeve spanning the vocal cords. In another example of using the invention, an inventive hydrated sleeve is on an endotracheal tube, with the sleeve spanning the vocal cords.

In practicing the invention, one or more inventive anti-VAP device(s) may be used alone, or with one or more anti-VAP material(s). The inventive anti-VAP methods, systems and devices may be used to reduce microaspiration, reduce oropharyngeal bacterial load, and/or to provide airway anesthesia.

In the inventive methods and in using the inventive devices and systems, optionally suctioning may be performed. For example, an anti-VAP device may be used that allows suctioning from around close proximity of the ETT (such as above the ETT balloon).

Example 9

Because a major source of VAP causing organisms can reside in and on the patient's dentition including the gums (gingival) and nearby mucosa, in this example, an inventive anti-VAP device (such as, e.g., an anti-VAP mouthpiece device 1900) is constructed for use in the oral cavity. Advantageously, use of an anti-VAP mouthpiece device in an intubated patient minimizes or avoids the need for the well-known and practiced nursing maneuver, directed at reducing VAP, of performance of repetitive dental and oral hygiene on the patient which involve brushing the patient's teeth and/or swabbing of the oral surfaces repetitively with antiseptic solutions such as chlorhexidine. The use of an anti-VAP mouthpiece device advantageously reduces this mentioned labor intensive effort while also providing more continuous antibacterial coverage of oral surfaces, which is a great benefit to the intubated patient as well as to the nursing and support staff.

Examples of materials useable for this anti-VAP mouthpiece device are, e.g., sponge materials, hydrogel materials, other materials described hereinabove for making an anti-VAP device, etc. Such materials may absorb oral secretions and provide antibacterial actions. They may also be presaturated and/or resaturated with antimicrobial agents such as chlorhexidine, hydrogen peroxide and other agents which can be released over time onto dental and mucosal surfaces.

In this example, the sponge or hydrogel material or other material for making an anti-VAP device is formed into a form of a mouthpiece which covers dental and proximal mucosal surfaces of an intubated patient. The anti-VAP mouthpiece device absorbs secretions, and preferably also kills bacteria and maintains oral and dental hygiene on a continuous basis.

The inventive anti-VAP mouthpiece device provided in this example conforms to the teeth and gingiva of the patient, along the lines of a mouthpiece worn by a football player or snorer. Preferably the mouthpiece covers most of the buccal, lip and sublingual/lingual mucosa of a patient as well as the hard and soft palate mucosa.

Optionally, portions of the mouthpiece may extend and come into contact with the deeper posterior pharynx as well.

The mouthpiece addresses the organisms and secretions from the gums and dentition of patients which are a major source of organisms.

Use of a mouthpiece device according to this example would greatly reduce the labor of carrying out oral hygiene in patients on a mechanical ventilator.

A preferred use of inventive anti-VAP mouthpiece devices is in intubated patients. Another use of inventive anti-VAP mouthpiece devices is in non-intubated patients such as nursing home patients to prevent aspiration pneumonia especially in patients whose oral hygiene is poor. This use may also enhance the overall oral hygiene of patients who cannot provide themselves, or be provided, routine oral hygiene. Use of the device may lead to improved oral and dental health.

Example 9A

Figure 19:
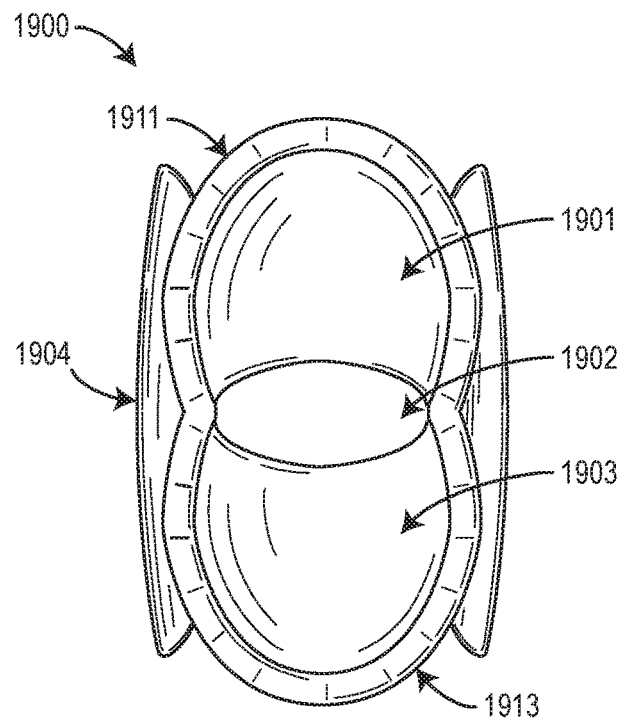
FIG. 19 is a side view of an inventive anti-VAP mouthpiece device 1900 in an open position.
Figure 19A:
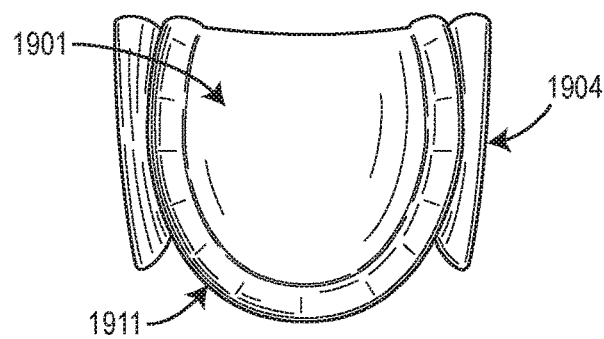
FIG. 19A is a top view of the inventive device 1900 of FIG. 19.
Figure 19B:
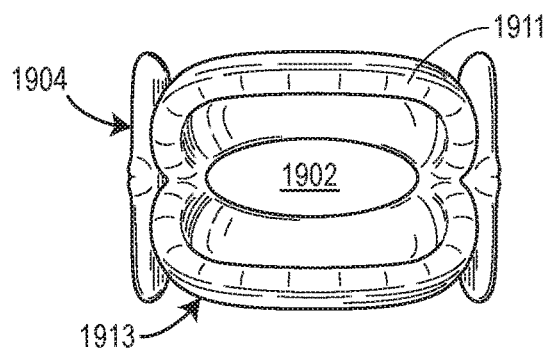
FIG. 19B is a front view of the inventive device 1900 of FIG. 19.

In this example, inventive anti-VAP mouthpiece device 1900 (FIGS. 19-19B) is provided comprising an upper plate 1901, center-hole 1902, lower plate 1903, upper segment 1911, lower segment 1913 and side wings 1904. Preferably the upper plate 1901 covers the patient's hard/soft palate surface. The upper segment 1911 receives the patient's upper dentition and gingival. Through an open center-hole 1902, passage is permitted of an endotracheal tube or nasogastric tube. Preferably the lower plate 1903 covers the patient's tongue surface. The lower segment 1913 receives the patient's lower dentition and gingival. Side wings 1904 cover buccal mucosa and preferably comprise an absorptive material.

Optionally, upper plate 1901 and lower plate 1903 can have segments (not shown) which extend backwards and into the deeper oropharynx without obstructing the center lumen.

For anti-device 1900, the bottom view (not shown) resembles the top view (FIG. 19A), except that instead of the upper plate 1901 and upper segment 1911 of the top view, the lower plate 1903 and lower segment 1913 would be seen.

Example 9B

In this example, an inventive anti-VAP mouthpiece device is made completely of a spongy and/or hydrogel absorptive material.

Example 9C

In this example, an inventive anti-VAP mouthpiece device is made of a relatively rigid material lined with a spongy and/or hydrogel absorptive material.

While the invention has been described in terms of its preferred embodiments, those skilled in the art will recognize that the invention can be practiced with modification within the spirit and scope of the appended claims.

What we claim as our invention is:

1. An anti-ventilator associated pneumonia (anti-VAP) mouthpiece device, comprising:
    an upper segment;
    a lower segment, wherein said upper segment and said lower segment are configured for arrangement in an oral cavity of a patient and form a barrier that blocks passage of VAP-causing secretions into a lower respiratory tract of said patient; and
    an absorbent material forming at least part of either or both said upper segment and said lower segment, said absorbent material being configured to absorb VAP-causing secretions from at least said oral cavity of said patient,
    wherein said upper segment and said lower segment define a center-hole configured to permit passage of an endotracheal tube (ETT) or a nasogastric tube and are configured so as not to obstruct a center pharyngeal lumen of said patient.

2. The anti-VAP mouthpiece device of claim 1, wherein said upper segment and said lower segment are configured to conform to dental and proximal mucosal surfaces of said oral cavity of said patient.

3. The anti-VAP mouthpiece device of claim 1, wherein said lower segment is configured to cover at least part of lower dentition and gingival of said patient.

4. The anti-VAP mouthpiece device of claim 1, wherein said lower segment includes a lower plate configured to cover a tongue of said patient.

5. The anti-VAP mouthpiece device of claim 1, wherein said upper segment is configured to cover at least part of upper dentition and gingival of said patient.

6. The anti-VAP mouthpiece device of claim 1, wherein said upper segment includes an upper plate configured to cover a hard/soft palate surface of said patient.

7. The anti-VAP mouthpiece device of claim 1, further comprising side wings configured to cover buccal mucosa of said patient.

8. The anti-VAP mouthpiece device of claim 7, wherein said side wings are comprised at least partly of absorbent material.

9. The anti-VAP mouthpiece device of claim 7, wherein the side wings have a first segment extending upwardly to cover an upper dental and mucosal region and a second segment extend downwardly to cover a lower dental and mucosal region.

10. The method anti-VAP mouthpiece device of claim 1, wherein said absorbent material is saturated with antimicrobials or medicinals for sustained contact and releaskey Currently amended e to at least one dentition or mucosal surface of said patient.

11. The anti-VAP mouthpiece device of claim 1, wherein said upper segment and said lower segment together form a solid member which is a one-size-fits-all shape installable in adult patients irrespective of tracheal diameter.

12. The anti-VAP mouthpiece device of claim 1, wherein said upper segment and said lower segment together form a solid member which is a one-size-fits-all shape installable in pediatric patients irrespective of tracheal diameter.

13. The anti-VAP mouthpiece device of claim 1, wherein the absorbent material comprises medicinals or antimicrobials.

14. The anti-VAP mouthpiece device of claim 13, wherein said absorbent material is saturated with antimicrobials, and said antimicrobials are selected from the group consisting of chlorhexidine and hydrogen peroxide.

15. The anti-VAP mouthpiece device of claim 1, wherein the absorbent material comprises an anesthetic agent.

16. The anti-VAP mouthpiece device of claim 1, wherein the absorbent material has capacity to absorb at least 0.1 ml or 0.1 gm of secretions.

17. The anti-VAP mouthpiece device of claim 1, wherein the absorbent material has capacity to absorb at least 1 ml or 1 gm of secretions.

* * * * *

UNITED STATES PATENT AND TRADEMARK OFFICE
CERTIFICATE OF CORRECTION

PATENT NO. : 10,751,494 B2
APPLICATION NO. : 15/274725
DATED : August 25, 2020
INVENTOR(S) : Kevin R. Ward et al.

Page 1 of 1

It is certified that error appears in the above-identified patent and that said Letters Patent is hereby corrected as shown below:

In the Claims

At Column 16, Line 52, "The method anti-VAP" should be -- The anti-VAP --.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*